US009926261B2

(12) United States Patent
LaVoie et al.

(10) Patent No.: US 9,926,261 B2
(45) Date of Patent: Mar. 27, 2018

(54) BACTERIAL EFFLUX PUMP INHIBITORS

(71) Applicant: Rutgers, The State University of New Jersey, New Brunswick, NJ (US)

(72) Inventors: Edmond J. LaVoie, New Brunswick, NJ (US); Ajit K. Parhi, New Brunswick, NJ (US); Gifty A. Blankson, New Brunswick, NJ (US); Malvika Kaul, New Brunswick, NJ (US); Daniel S. Pilch, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/066,911

(22) Filed: Mar. 10, 2016

(65) Prior Publication Data

US 2016/0271082 A1 Sep. 22, 2016

Related U.S. Application Data

(60) Provisional application No. 62/133,162, filed on Mar. 13, 2015, provisional application No. 62/131,124, filed on Mar. 10, 2015.

(51) Int. Cl.

| | |
|---|---|
| ***C07C 233/00*** | (2006.01) |
| ***A61K 31/165*** | (2006.01) |
| ***C07C 233/78*** | (2006.01) |
| ***A61K 45/06*** | (2006.01) |

(52) U.S. Cl.

CPC ............ *C07C 233/78* (2013.01); *A61K 45/06* (2013.01)

(58) Field of Classification Search

CPC .... C07C 235/34; A61K 31/165; A61K 31/166

USPC .......................................... 564/161; 514/617

See application file for complete search history.

(56) References Cited

U.S. PATENT DOCUMENTS

| | | | |
|---|---|---|---|
| 4,938,949 | A | 7/1990 | Borch et al. |
| 2016/0271081 | A1 | 9/2016 | Lavoie et al. |

OTHER PUBLICATIONS

STN CAS Registry File, RN 788126-67-0, 2004.*

STN CAS Registry File, RN 860554-34-3, 2005.*

STN CAS Registry File, RN 1026060-58-1.*

* cited by examiner

*Primary Examiner* — Shengjun Wang

(74) *Attorney, Agent, or Firm* — Viksnins Harris Padys Malen LLP

(57) ABSTRACT

Disclosed herein are compounds of formula I:

I

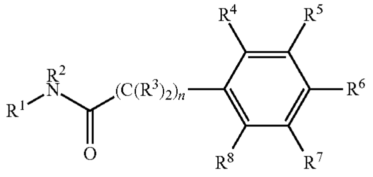

and salts thereof. Also disclosed are compositions comprising of compounds of formula I and methods using compounds of formula I.

24 Claims, 2 Drawing Sheets

BACTERIAL EFFLUX PUMP INHIBITORS

PRIORITY OF INVENTION

This application claims priority from U.S. Provisional Patent Application Nos. 62/131,124 filed Mar. 10, 2015 and 62/133,162 filed Mar. 13, 2015, which applications are hereby incorporated by reference in their entirety.

BACKGROUND OF THE INVENTION

Antibiotics have been effective tools in the treatment of infectious diseases. However, bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with a known antibiotic, lower the minimum inhibitory concentration of the known antibiotic to inhibit bacterial cell growth. Not to be bound by theory the compounds are believed to exert this effect by the inhibition of a bacterial efflux pump(s).

Accordingly, one embodiment provides a compound of formula I:

I

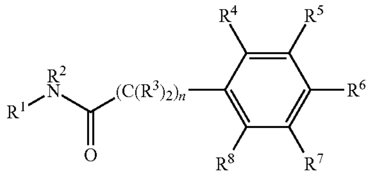

wherein:

$R^1$ is $(C_3\text{-}C_8)$alkyl substituted with two or more (e.g., 2, 3 or 4) groups selected from $—NR^{b1}R^{c1}$, $—NHNH_2$, $—C(=NR^{a1})(NR^{b1}R^{c1})$, $—NR^{a1}C(=NR^{a1})(R^{d1})$ and $—NR^{a1}C(=NR^{a1})(NR^{b1}R^{c1})$;

$R^2$ is hydrogen or $(C_1\text{-}C_3)$alkyl;

each $R^3$ is independently hydrogen, halo or $(C_1\text{-}C_4)$alkyl;

$R^4$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^5$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^6$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^7$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^8$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

each $R^{a1}$ is independently hydrogen or $(C_1\text{-}C_4)$alkyl;

each $R^{b1}$ and $R^{c1}$ is independently hydrogen or $(C_1\text{-}C_4)$alkyl;

$R^{d1}$ is $(C_1\text{-}C_3)$alkyl and n is 0 or 1;

or a salt thereof.

One embodiment provides a pharmaceutical composition comprising a compound of formula I as described herein or a pharmaceutically acceptable salt thereof, and a pharmaceutically acceptable vehicle.

One embodiment provides pharmaceutical composition comprising a compound of formula I as described herein or a pharmaceutically acceptable salt thereof, one or more antibacterial agents and a pharmaceutically acceptable vehicle.

One embodiment provides a method of inhibiting a bacterial efflux pump in an animal (e.g., a mammal such as a human) comprising administering to the animal a compound of formula I as described herein, or a pharmaceutically acceptable salt thereof.

One embodiment provides a method of inhibiting a bacterial efflux pump in an animal (e.g., a mammal such as a human) comprising administering to the animal in need thereof a compound of formula I as described herein, or a pharmaceutically acceptable salt thereof.

One embodiment provides method of treating or preventing a bacterial infection in an animal (e.g., a mammal such as a human) comprising co-administering to the animal a compound as described herein, or a pharmaceutically acceptable salt thereof and one or more antibacterial agents.

One embodiment provides method of treating or preventing a bacterial infection in an animal (e.g., a mammal such as a human) comprising co-administering to the animal in need thereof a compound as described herein, or a pharmaceutically acceptable salt thereof and one or more antibacterial agents.

One embodiment provides a method of inhibiting a bacterial efflux pump in an animal (e.g., a mammal such as a human) with a bacterial infection comprising administering to the animal a compound of formula I as described herein, or a pharmaceutically acceptable salt thereof.

One embodiment provides method of treating or preventing a bacterial infection in an animal (e.g., a mammal such as a human) infected with bacteria comprising co-administering to the animal a compound of formula I as described herein, or a pharmaceutically acceptable salt thereof and one or more antibacterial agents.

One embodiment provides a compound of formula I as described herein, or a pharmaceutically acceptable salt thereof for use in medical treatment.

One embodiment provides a compound of formula I as described herein or a pharmaceutically acceptable salt thereof for the prophylactic or therapeutic inhibition of a bacterial efflux pump for the treatment of a bacterial infection.

One embodiment provides a compound of formula I as described herein or a pharmaceutically acceptable salt thereof which is used in combination with one or more antibacterial agents for the prophylactic or therapeutic treatment of a bacterial infection.

One embodiment provides the use of a compound of formula I as described herein or a pharmaceutically acceptable salt thereof for the preparation of a medicament for inhibiting a bacterial efflux pump.

One embodiment provides the use of a compound of formula I as described herein or a pharmaceutically acceptable salt thereof for the preparation of a medicament for treating a bacterial infection in an animal (e.g., a mammal such as a human).

One embodiment provides the use of a compound of formula I as described herein or a pharmaceutically acceptable salt thereof for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

Figure 1:
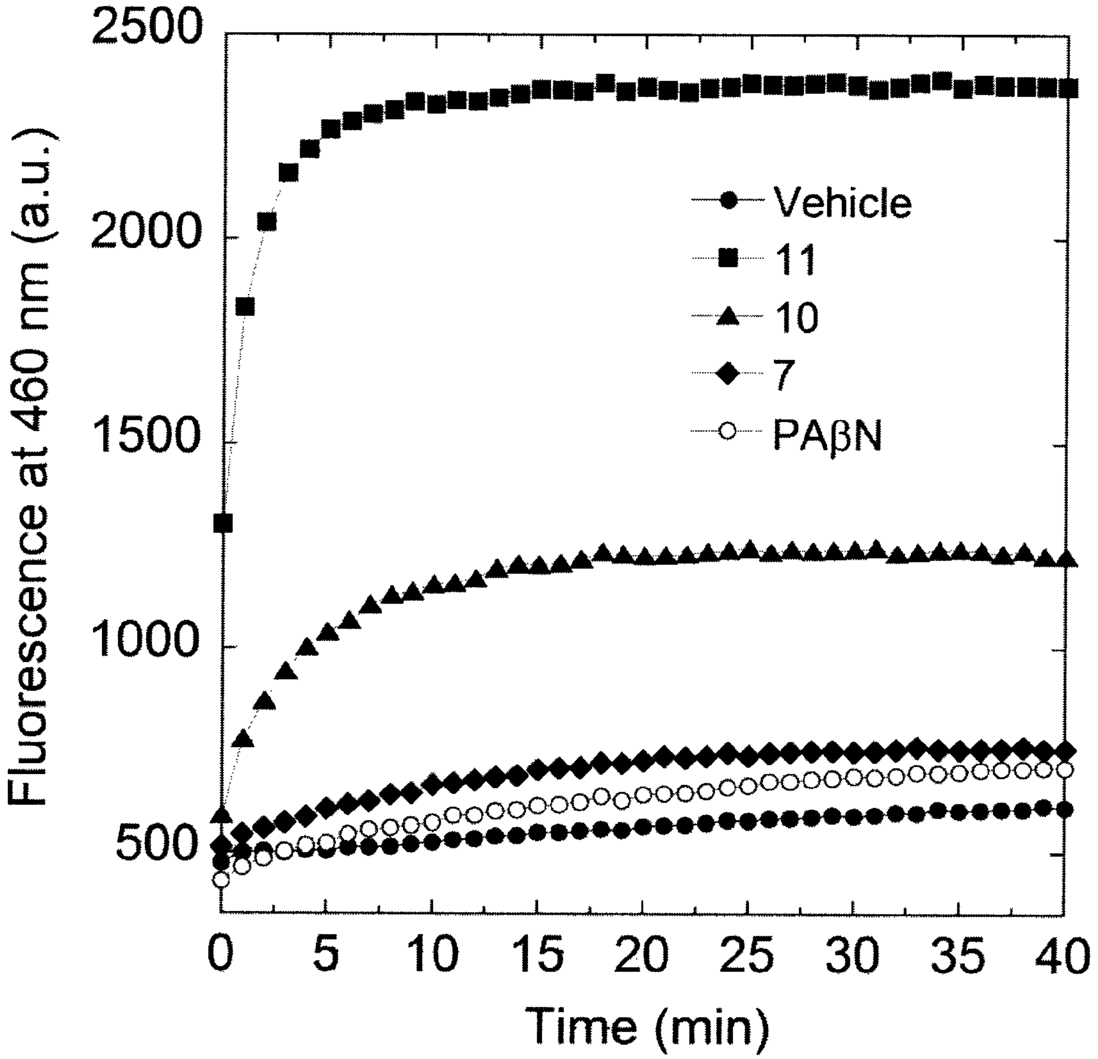
FIG. 1 illustrates representative fluorescence profiles for a number of compounds with activity as efflux pump inhibitors (EPIs of the Examples). The compounds cause increased accumulation of Hoechst 33342 dye inside the bacteria, where the dye binds to the bacterial DNA. This binding reaction results in a substantial increase in fluorescence emission relative to vehicle (DMSO) control.
Figure 2:
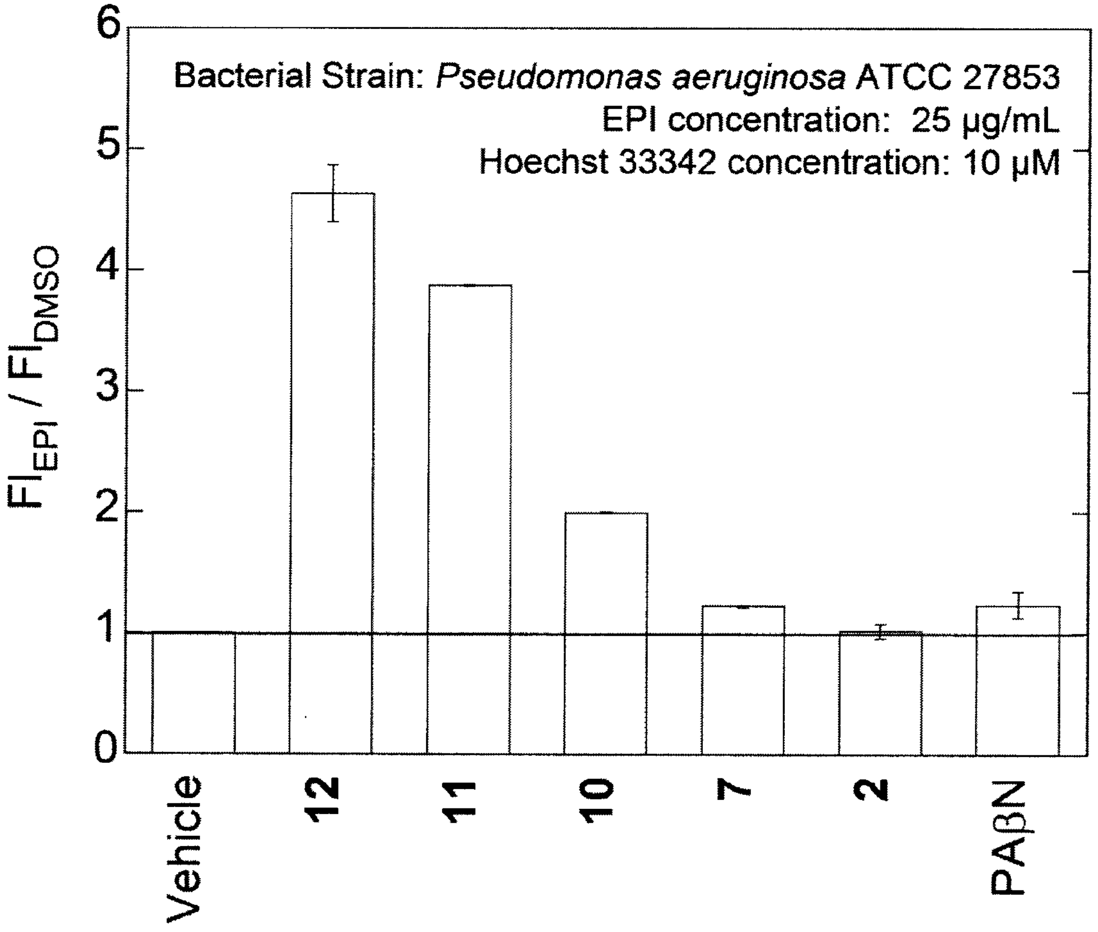
FIG. 2 illustrates the ratio of Hoechst 33342 fluorescence in the presence of an efflux pump inhibitors (EPIs of the Examples) to that in the presence of DMSO vehicle (FlEPI/FlDMSO). A FlEPI/FlDMSO ratio of 1 (the horizontal line the graph) indicates insignificant EPI-induced increase in Hoechst fluorescence (i.e., no EPI activity). By contrast, a FlEPI/FlDMSO ratio >1 reflects an EPI-induced increase in Hoechst 33342 fluorescence, and thus an EPI-induced increase in the accumulation of Hoechst 33342 inside the bacteria.

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "($C_a$-$C_b$)alkyl" wherein a and b are integers refers to a straight or branched chain alkyl (hydrocarbon) radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$ haloalkyl".

The term "alkoxy" refers to —O(alkyl) and the term "haloalkoxy" refers to an alkoxy that is substituted with one or more (e.g., 1, 2, 3, or 4) halo.

The term cycloalkyl includes saturated and partially unsaturated carbocyclic ring systems. In one embodiment the cycloalkyl is a monocyclic carbocyclic ring. One such cycloalkyl is a "$(C_3-C_8)$cycloalkyl".

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; $(C_1-C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is to be understood that the embodiments provided below are for compounds of formula I and all sub-formulas thereof (e.g., formulas Ia, Ib, Ic, Id, Ie, If, Ig). It is to be understood the two or more embodiments may be combined.

In one embodiment $R^2$ is hydrogen.

In one embodiment $R^3$ is hydrogen.

One embodiment provides a compound of formula Ia:

Ia

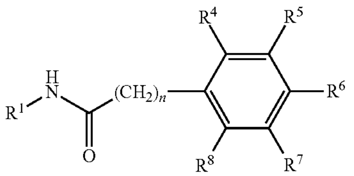

or a salt thereof.

In one embodiment $R^8$ is hydrogen.

In one embodiment $R^4$ is hydrogen, $(C_1-C_6)$haloalkyl or aryl wherein the aryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^4$ is hydrogen, —$CF_3$ or phenyl.

In one embodiment $R^4$ is hydrogen.

One embodiment provides a compound of formula Ib:

Ib

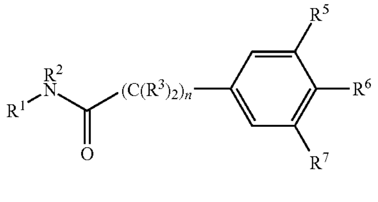

or a salt thereof.

In one embodiment $R^7$ is hydrogen.

One embodiment provides a compound of formula Ic:

Ic

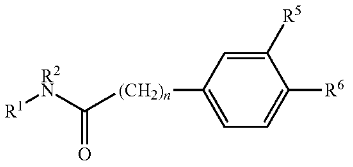

or a salt thereof.

In one embodiment $R^5$ is halo, $(C_1-C_6)$alkyl, $(C_1-C_6)$ haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$ haloalkyl, $(C_1-C_4)$alkoxy and $(C_1-C_4)$haloalkoxy;

In one embodiment $R^5$ is $(C_1-C_6)$haloalkyl.

In one embodiment $R^5$ —$CF_3$.

In one embodiment $R^6$ is halo, $(C_1-C_6)$alkyl, $(C_1-C_6)$ haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$ haloalkyl, $(C_1-C_4)$alkoxy and $(C_1-C_4)$haloalkoxy;

In one embodiment $R^6$ is $(C_1-C_6)$haloalkyl.

In one embodiment $R^6$ —$CF_3$.

In one embodiment $R^6$ is hydrogen.

One embodiment provides a compound formula Id:

Id

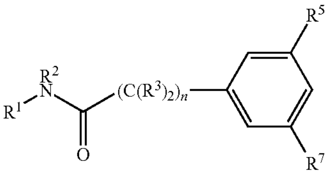

or a salt thereof.

One embodiment provides a compound of formula Ie:

Ie

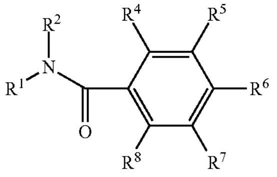

or a salt thereof.

One embodiment provides a compound of formula If:

If

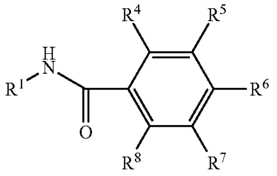

or a salt thereof.

One embodiment provides a compound of formula Ig:

Ig

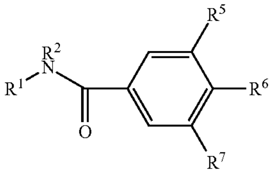

or a salt thereof.

In one embodiment $R^5$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^5$ is $(C_1\text{-}C_6)$alkyl, $(C_1\text{-}C_6)$haloalkyl, or aryl wherein the aryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^5$ is $(C_1\text{-}C_6)$alkyl, $(C_1\text{-}C_6)$haloalkyl, or phenyl wherein phenyl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^5$ is tert-butyl, —$CF_3$, phenyl or 4-fluorophenyl.

In one embodiment $R^7$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^7$ is $(C_1\text{-}C_6)$alkyl, $(C_1\text{-}C_6)$haloalkyl or aryl wherein the aryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^7$ is $(C_1\text{-}C_6)$alkyl, $(C_1\text{-}C_6)$haloalkyl, or phenyl wherein phenyl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^7$ is tert-butyl, —$CF_3$, phenyl or 4-fluorophenyl.

In one embodiment the moiety:

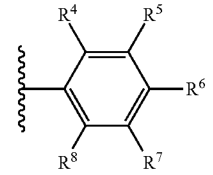

of the compound of formula I is:

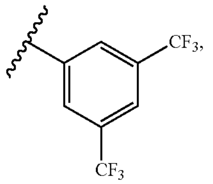

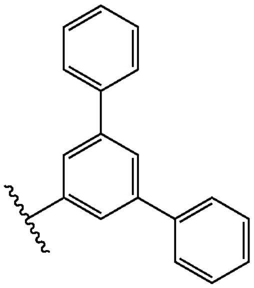
,

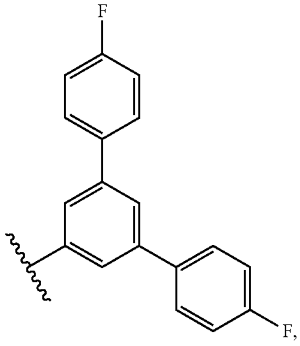

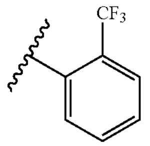
,

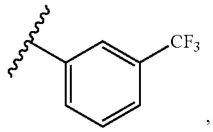
,

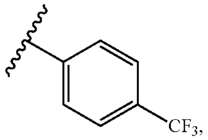

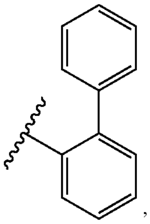
,

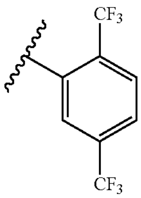
,

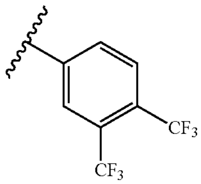
or

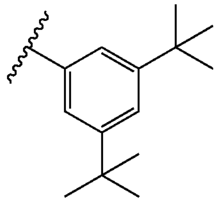
.

In one embodiment $R^1$ is $(C_3$-$C_8)$alkyl substituted with two or more groups independently selected from —$NR^{b1}R^{c1}$.

In one embodiment $R^1$ is $(C_3$-$C_8)$alkyl substituted with two groups independently selected from —$NR^{b1}R^{c1}$.

In one embodiment $R^1$ is $(C_4$-$C_5)$alkyl substituted with two groups independently selected from —$NR^{b1}R^{c1}$.

In one embodiment $R^{b1}$ and $R^{c1}$ are each hydrogen.

In one embodiment $R^1$ is:

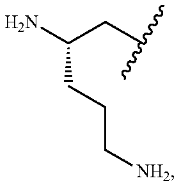
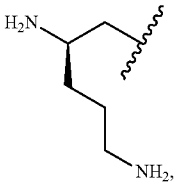
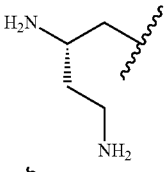
,
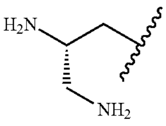
,
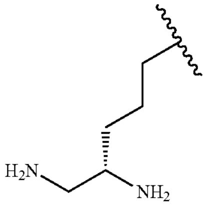
or
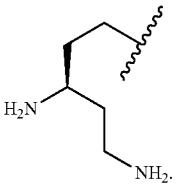

In one embodiment $R^1$ is:

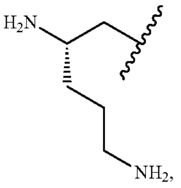
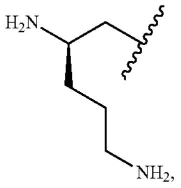
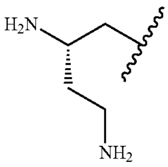
, or
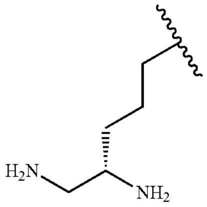
.

In one embodiment n is 0.

In one embodiment the compound of formula I is:

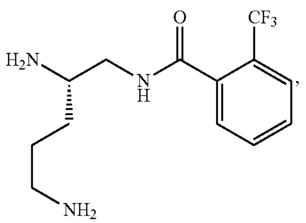

-continued

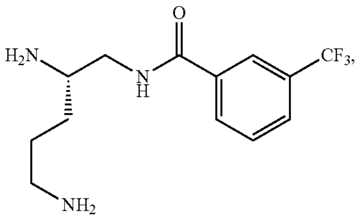
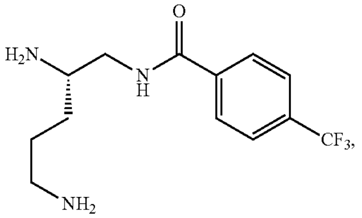
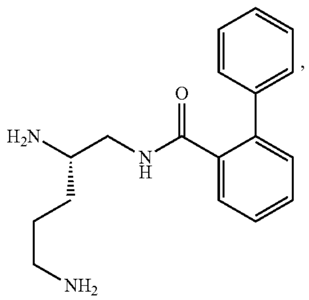
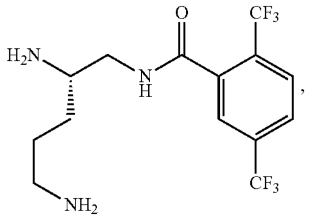
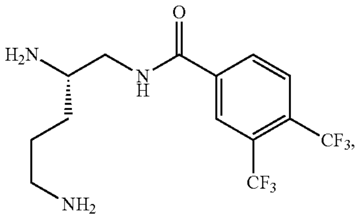
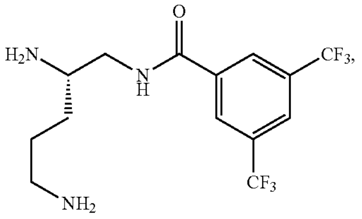
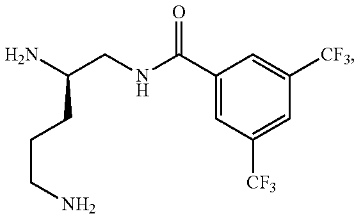

-continued
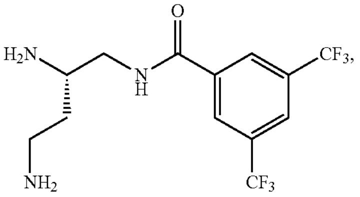
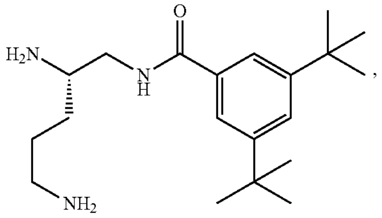
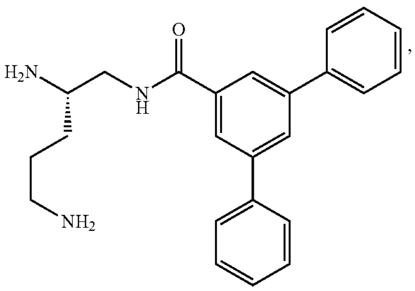
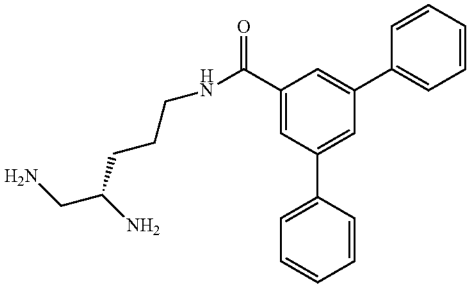
or
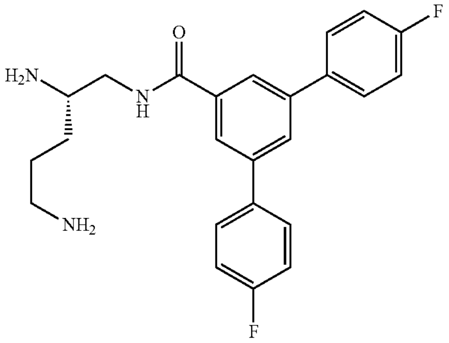 [SMILES: NCCC[C@H](N)CNC(=O)c1cc(-c2ccc(F)cc2)cc(-c2ccc(F)cc2)c1]
or a salt thereof.
In one embodiment the compound of formula I is:
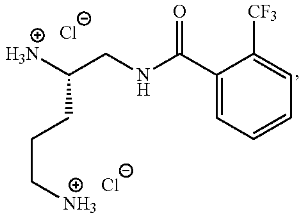
-continued
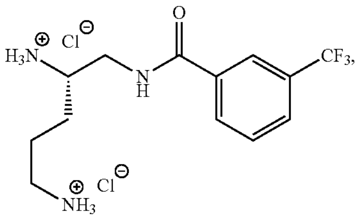
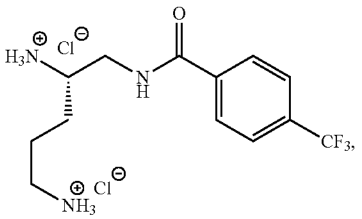
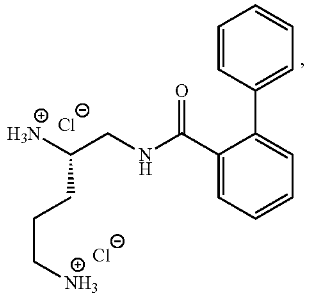
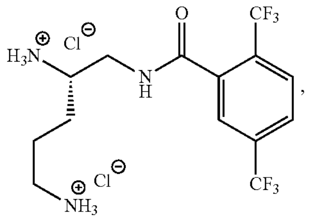
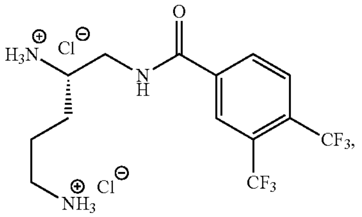
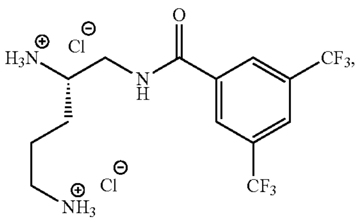
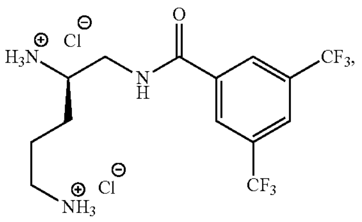

-continued

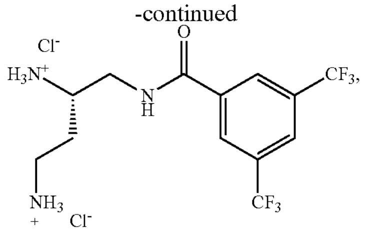

,

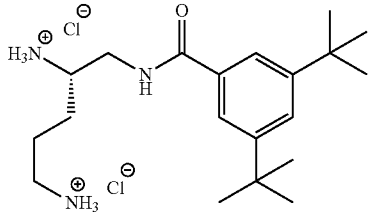

,

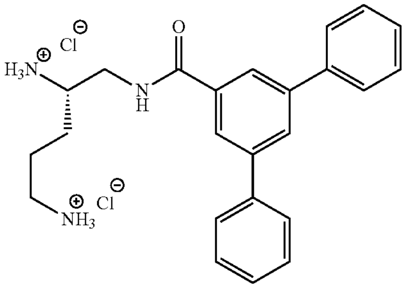

,

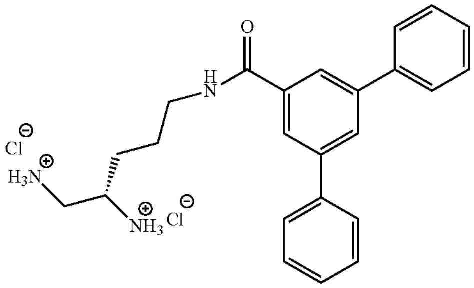

or

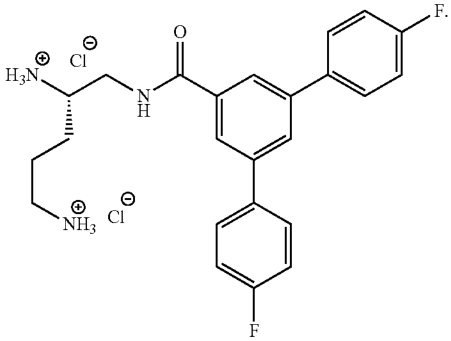 [SMILES: [NH3+]CCC[C@H]([NH3+])CNC(=O)c1cc(-c2ccc(F)cc2)cc(-c2ccc(F)cc2)c1 ; [Cl-] ; [Cl-]]

Generally, compounds of formula I as well as synthetic intermediates that can be used for preparing compounds of formula I can be prepared as illustrated in the following General Methods and Schemes. It is understood that variable groups shown below (e.g., $R^1$, $R^2$, $R^3$, $R^4$, $R^5$, $R^6$, $R^7$, $R^8$, n)) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Scheme I General Method for the Synthesis of Compounds of Formula I

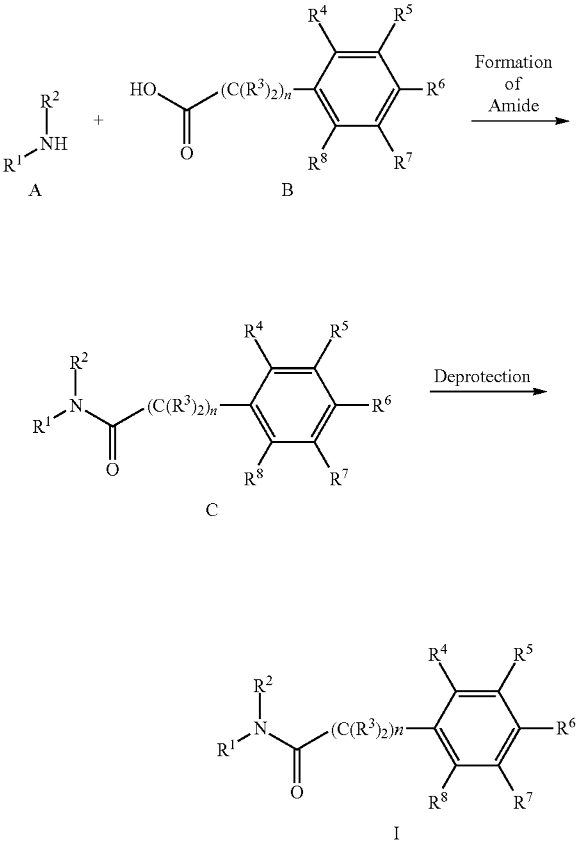

Reaction of the amine A with carboxylic acid B under standard coupling conditions provides intermediate C. Intermediate C can be deprotected to provide the compound of formula I. For instance, when $R^1$ of intermediate C includes a Cbz protected amine the Cbz group can be removed under hydrogenation conditions (e.g., Pd/C, $H_2$).

A particular protected intermediate useful in Scheme 1 is protected intermediate A which is:

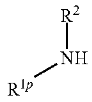

wherein $R^2$ has the values described herein for formula I and $R^{1p}$ is $(C_3$-$C_8)$alkyl substituted with two or more (e.g., 2, 3 or 4) —$NR^{b1}R^{c1}$ groups; each $R^{b1}$ and $R^{c1}$ is independently hydrogen or $(C_1$-$C_4)$alkyl wherein at least one of each $R^{b1}$ or $R^{c1}$ is a protecting group. In one embodiment the protecting group is a carbonyl benzyloxy (Cbz) group. In another embodiment one or more of the protecting groups can be benzyl (Bn) or t-butoxycarbonyl (Boc). Several known methods are available for the preparation of the desired protected amine intermediates.

One possible synthetic route to the formation of such intermediates is illustrated in the following general synthetic Scheme 2. In one embodiment each R is independently hydrogen or methyl.

Scheme 2 A Method that can be used for the Formation of a Di-protected Alkyltriamine

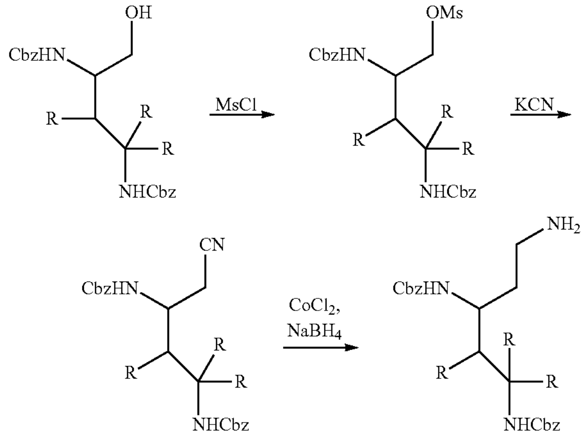

Scheme 3 illustrates a method that can be used for the formation of a general intermediate that can be employed in a wide variety of transformations, as illustrated in Scheme 4 to provide compounds of Formula 1.

Scheme 3 A Method that can be used for the Formation of a Versatile Intermediate

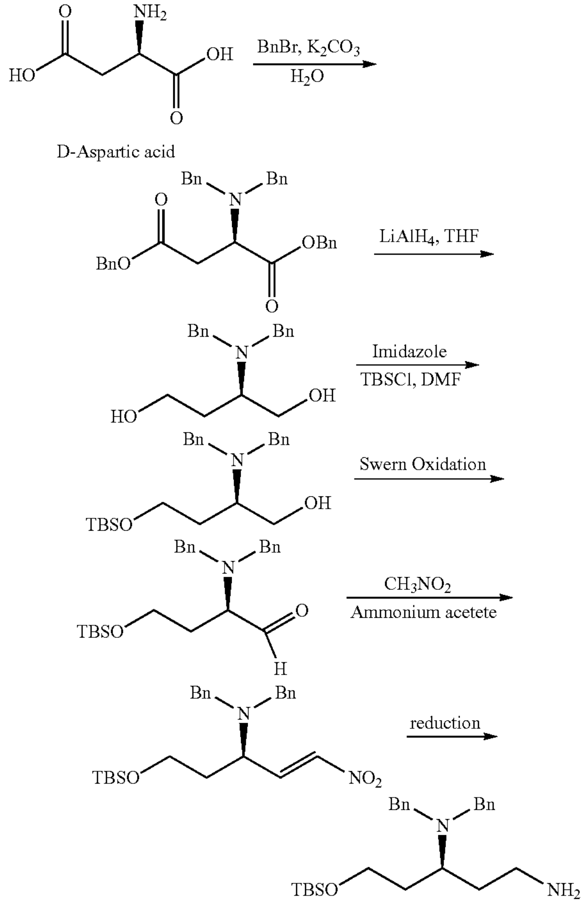

Scheme 4 Illustration of the use of the Versatile Intermediate in Scheme 3 that can be used to Prepare Compounds of Formula 1

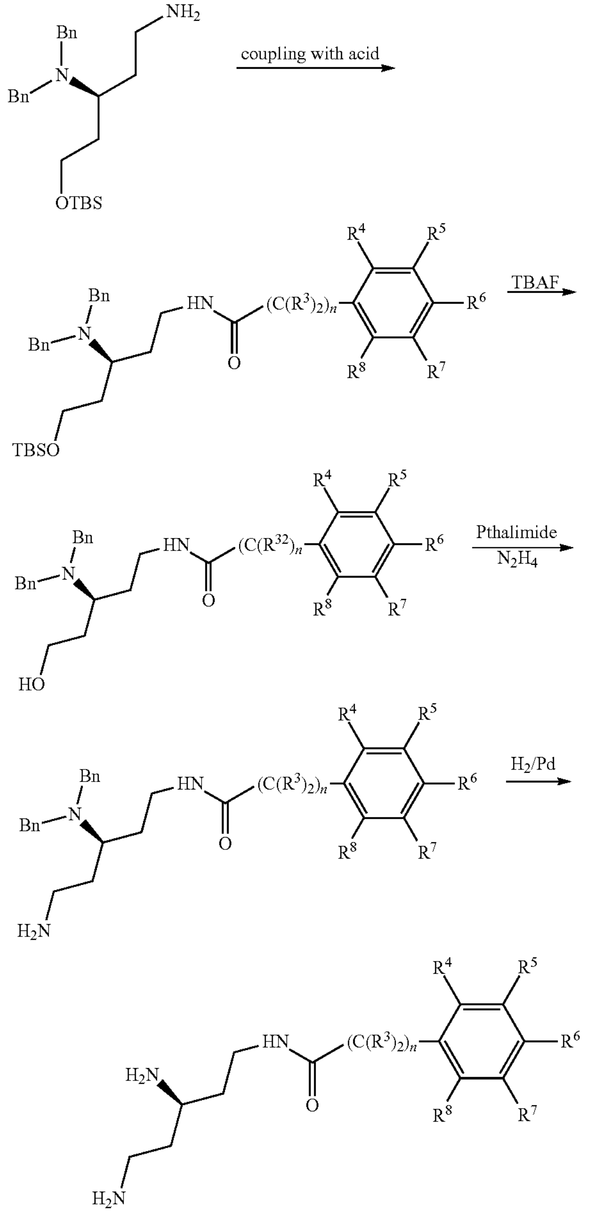

Illustration of the Use of Intermediate in Scheme 3 to Prepare a Compound of Formula 1

The flexibility in the chemistry that can be used to prepare compounds of Formula I is illustrated in Schemes 5a-d. The preparations depicted in these schemes use the intermediate shown in Scheme 3 with the structure:

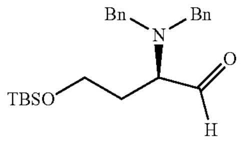 [SMILES: CC(C)(C)[Si](C)(C)OCC[C@H](C=O)N(Cc1ccccc1)Cc1ccccc1]

and related compounds with the structure:
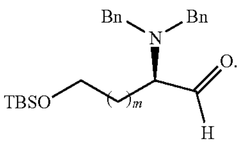
Schemes 5a to 5d
Examples of the use of the Intermediate in Scheme 3 that can be used for the Preparation of Compounds of Formula 1.
Scheme 5a
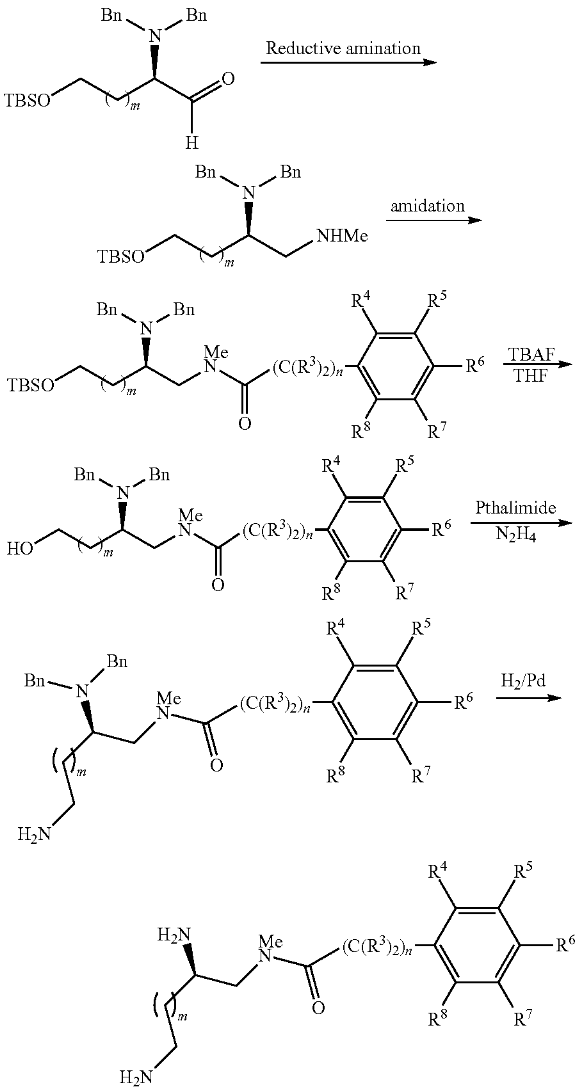
In one embodiment m is 0, 1, 2, 3, 4 or 5 (Scheme 5a). In one embodiment m is 1 (Scheme 5a).
Scheme 5b
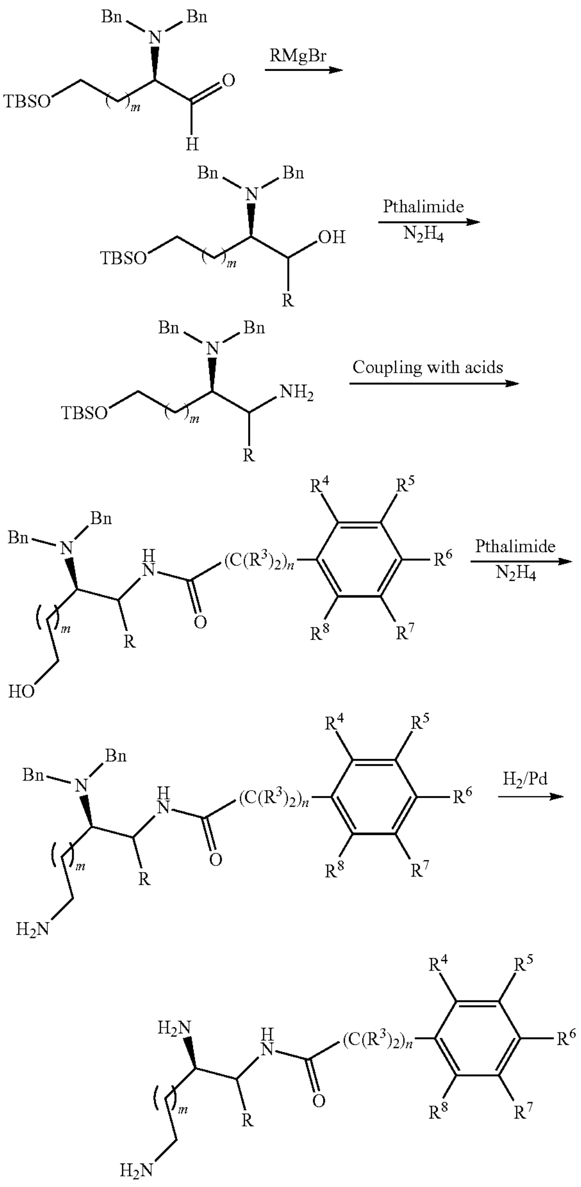
In one embodiment m is 0, 1, 2, 3 or 4 and R is methyl (Scheme 5b). In one embodiment m is 1 and R is methyl (Scheme 5b).
Scheme 5c
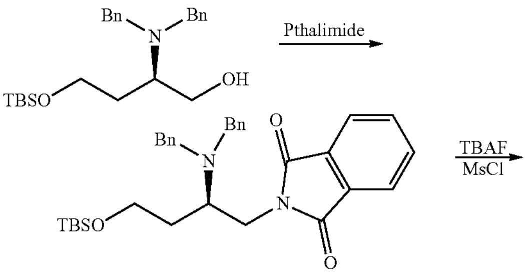

-continued

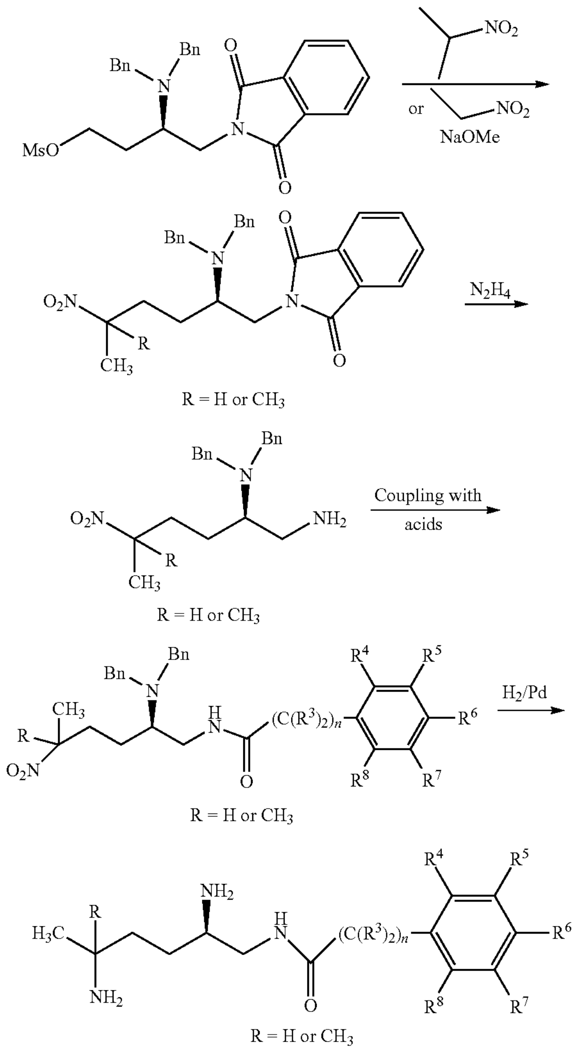

Scheme 5d

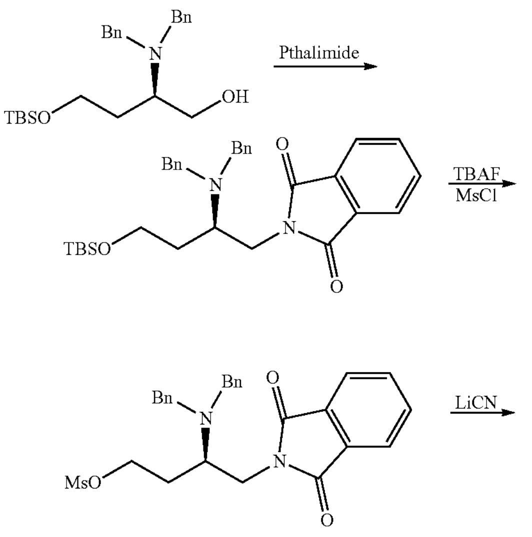

-continued

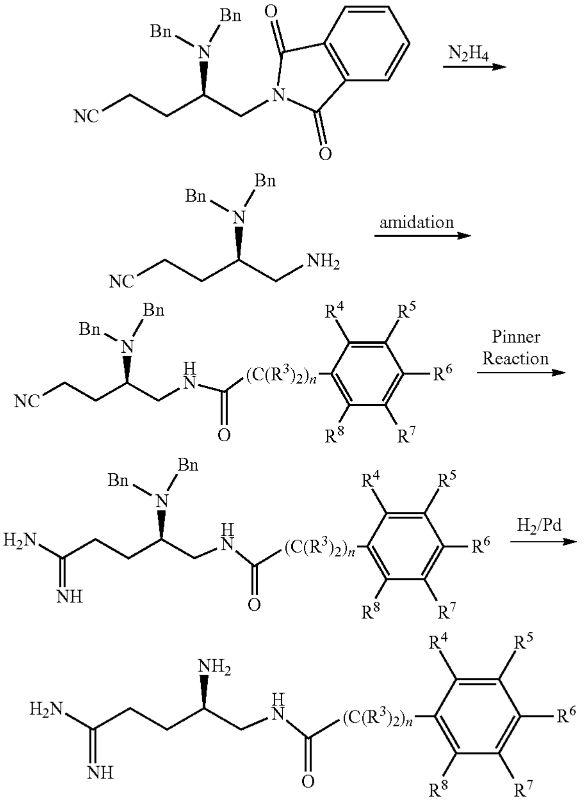

Methods for the preparation of a guanidine substituent from amine are well established. Synthetic Scheme 6 provides a method that employs one of the intermediates used in the listed examples which can be used to prepare additional compounds of formula I.

Scheme 6 General Method that can be used for the Preparation of a Guanidine Compounds of Formula I (from an amine)

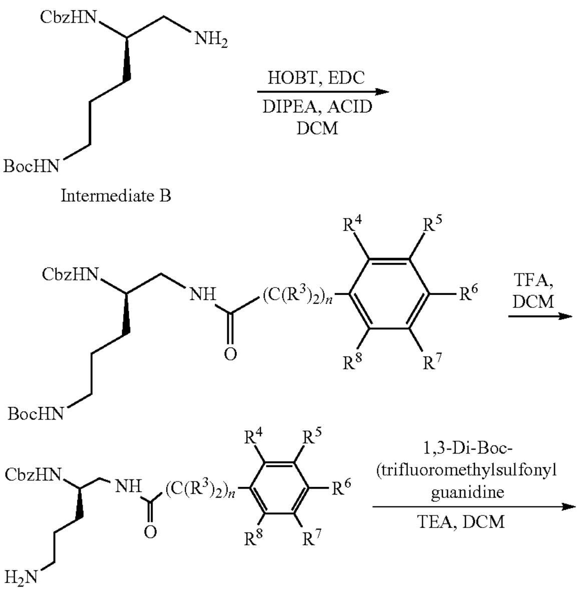

-continued

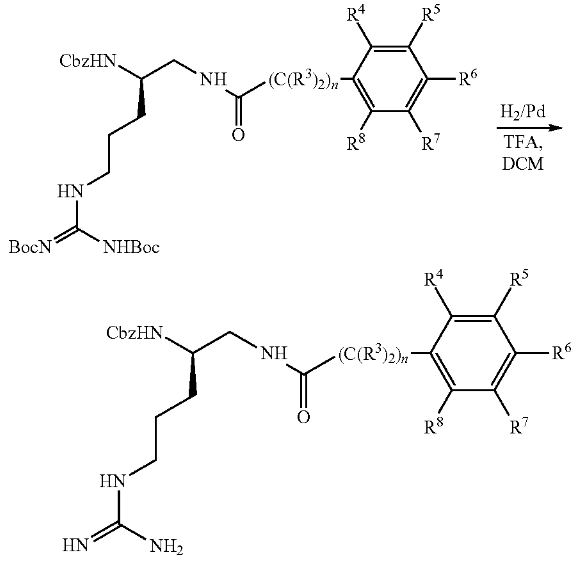

Similarly, one can prepare analogs that have the hydrazine moiety. Methods that can be used for the preparation of such analogs are illustrated in Scheme 7.

Scheme 7 General Method that can be used for the Preparation of Hydrazine Compounds of Formula I (from an amine)

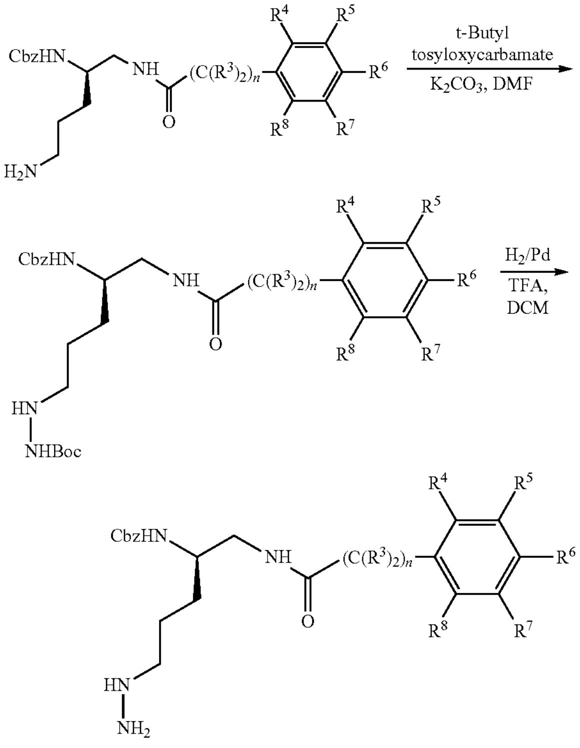

The preparation of amidine derivatives on the N-alkyl portion of the amides of Formula I are also readily accessible using standard chemistry that is well known in the art. An example of such an approach is outlined in Scheme 8.

Scheme 8 General Method that can be used for the Preparation of Amidine Compounds of Formula 1

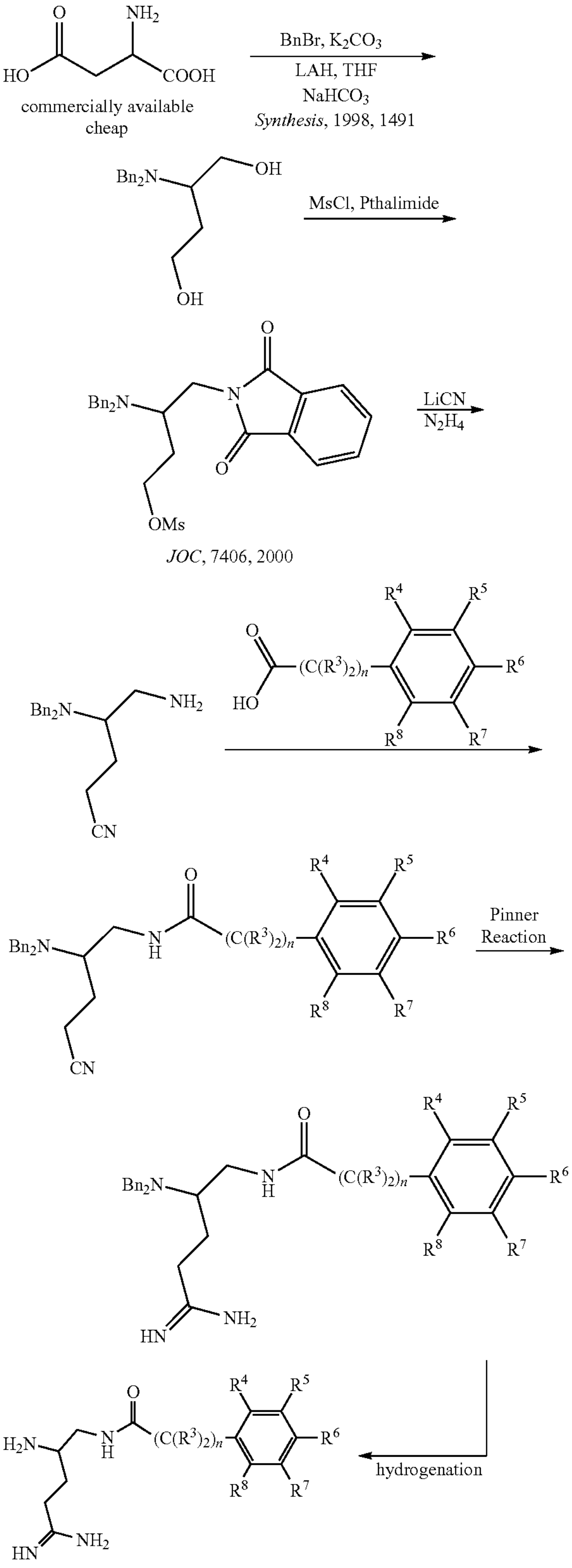

In a similar manner, the reversed amidine derivative of various structurally-related carboxamides can also be prepared as illustrated in Scheme 9.

Scheme 9 General Method that can be used for the Preparation of Reversed Amidine Compounds of Formula 1

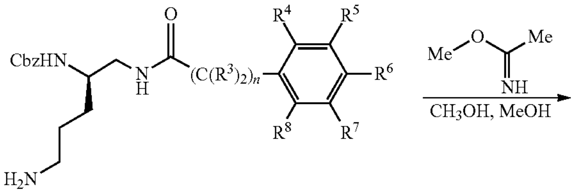

-continued

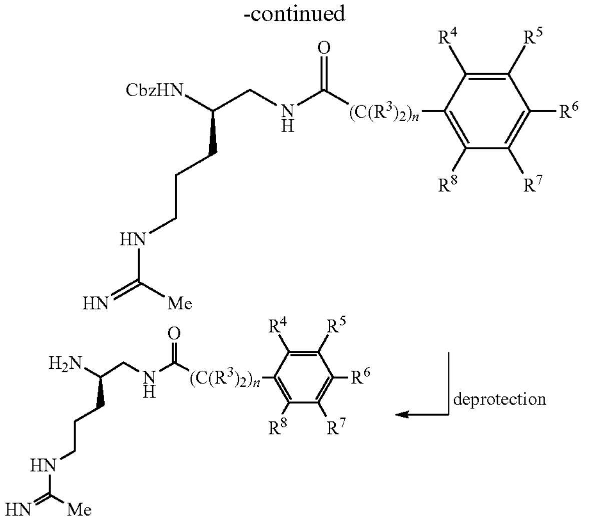

It is also well known in the art that primary amines can be converted to secondary amines by well-established methods and that both primary and secondary amines can be converted to their tertiary amines by standard methods as illustrated in Scheme 10.

Scheme 10 General Method that can be used for the Formation of Secondary and Tertiary Amine Compound of Formula 1.
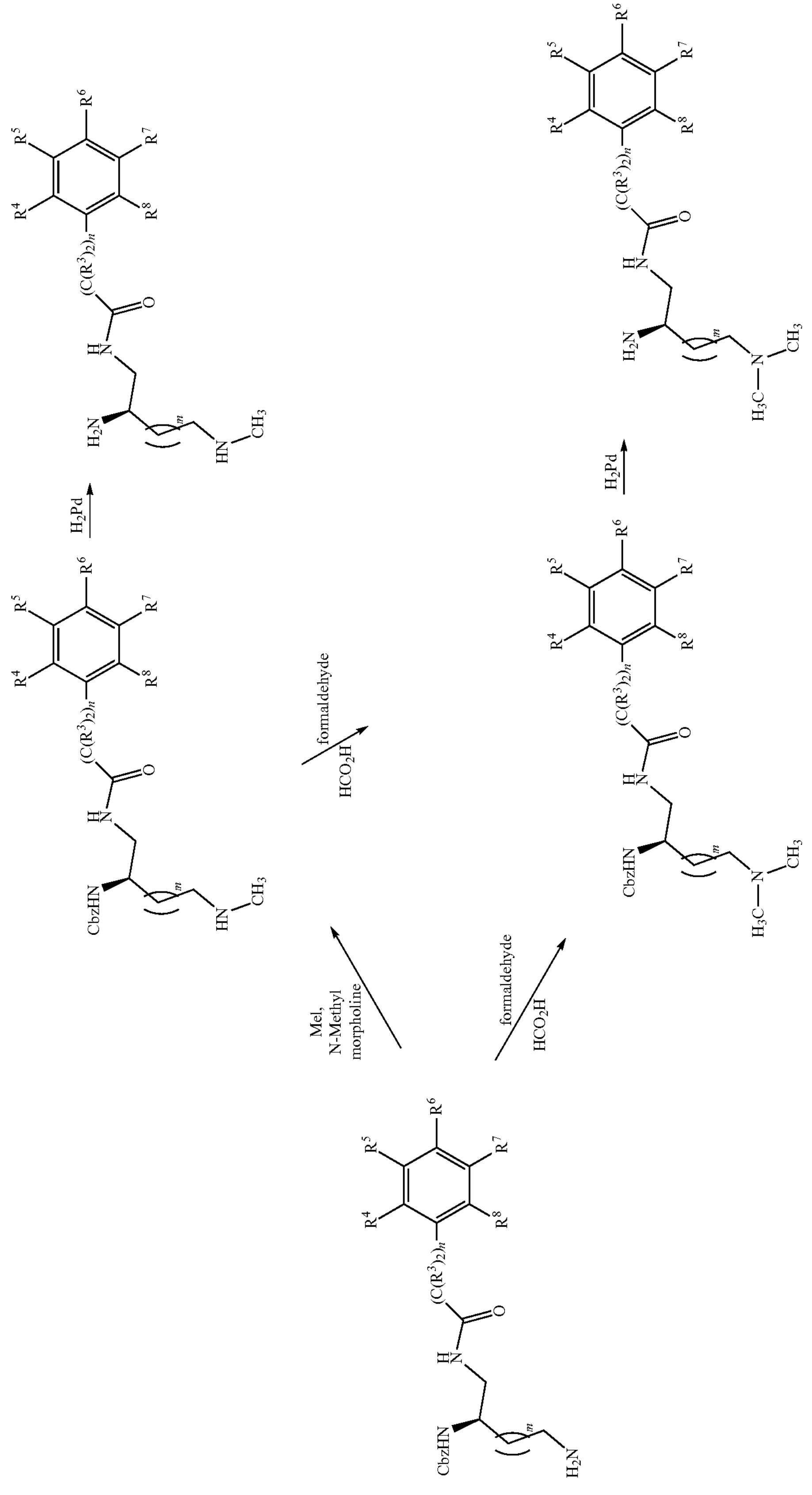

-continued
Scheme 10 General Method that can be used for the Formation of Secondary and Tertiary Amine Compound of Formula 1.
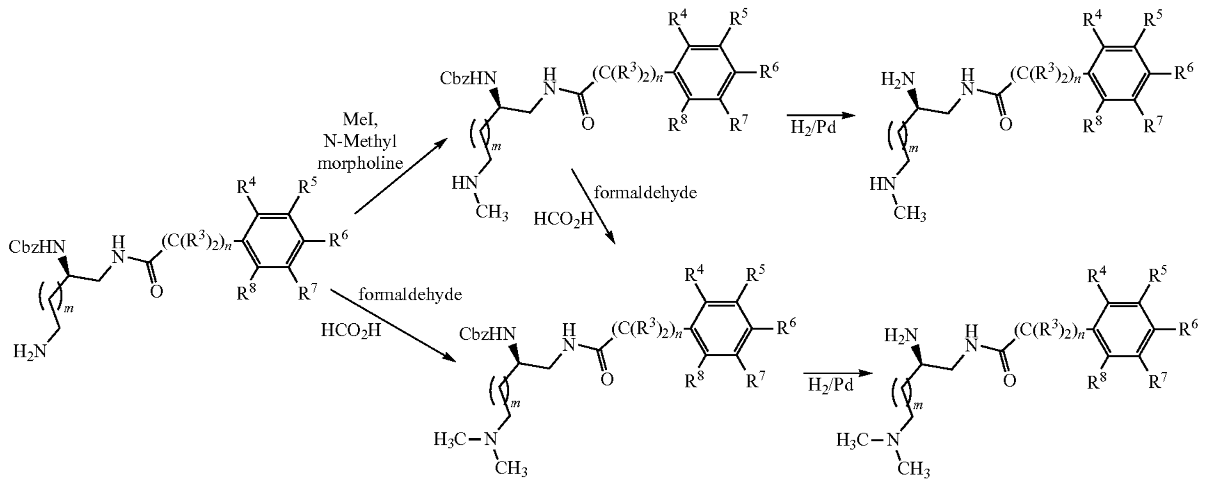

In one embodiment m is 0, 1, 2, 3, 4 or 5 (Scheme 10).

The compounds disclosed herein are bacterial efflux pump inhibitors. An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis*.

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracia, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis*.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, rifamycins, macrolides, ketolides, oxazolidinones, coumermycins, and chloramphenicol.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(═O)H in a compound of formula (I) could exist in tautomeric form as —N═C(OH)H. The present invention encompasses all tautomeric forms of a compound of formula I as well as mixtures thereof that can exist in equilibrium with non-charged and charged entities depending upon pH, which possess the useful properties described herein.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, p-$CH_3C_6H_4$ $SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method like Test A or Test B described below.

Test A. Minimum Inhibitory Concentration (MIC)-Based Assay for Efflux Pump Inhibition:

MIC-based assays were used to evaluate the impact of potential efflux pump inhibiting (EPI) compounds on the MIC of minocycline, an antibiotic known to be a substrate for Gram-negative bacterial efflux pumps. The assays were conducted in accordance with Clinical and Laboratory Standards Institute (CLSI) guidelines for broth microdilution, with the modification that assays were conducted in the presence and absence of the test EPI compounds. When present, the EPI compounds were added to cation-adjusted Mueller-Hinton (CAMH) broth (Becton, Dickinson and Co., Franklin Lakes, N.J.) at a final concentration of 12.5 μg/mL.

Log-phase Gram-negative bacteria were added to 96-well microtiter plates (at $5\times10^5$ colony forming units (CFU) per mL) containing two-fold serial dilutions of minocycline in CAMH broth either in the absence or presence of the test EPI compounds. In all assays, each serial dilution of minocycline was present in duplicate. The final volume in each well was 0.1 mL, and the microtiter plates were incubated aerobically for 24 hours at 37° C. Bacterial growth was then monitored by measuring the optical density (OD) at 600 nm using a VersaMax® plate reader (Molecular Devices, Inc., Sunnyvale, Calif.), with the MIC being defined as the lowest compound concentration at which growth was ≥90% inhibited compared to antibiotic-free control. The following Gram-negative bacterial strains were included in these assays:

*Escherichia coli* W4573, ATCC 25922, and ATCC BAA-201 (an extended spectrum β-lactamase (ESBL)-producing strain that expresses the TEM-3 β-lactamase).

*Klebsiella pneumoniae* ATCC 13883 and ATCC 700603 (an ESBL-producing strain that expresses the SHV-18 β-lactamase).

*Pseudomonas aeruginosa* ATCC 27853.

The efflux pump mutant *E. coli* strain N43 (acrA1) was used as a positive control.

Results from this test using *Escherichia coli* W4573 are shown in Table 1, which shows the enhancement of the MIC of minocycline in the presence of test compound using *Escherichia coli* W4573. The enhancement is the ratio of the minocycline MIC in the absence of test compound to the minocycline MIC in the presence of test compound.

Test B. Fluorescence-Based Hoechst 33342 Accumulation Assay for Efflux Pump Inhibition:

The impact of potential EPI compounds on the activity of efflux pumps was also evaluated with a fluorescence-based assay that measures the intrabacterial accumulation of Hoechst 33342, a known substrate of Gram-negative bacterial efflux pumps. Upon entering bacterial cells and binding to the bacterial DNA, Hoechst fluoresces brightly at 460 nm.

Bacterial cells were harvested from overnight cultures by centrifugation, and the cell pellet was washed with phosphate-buffered saline (PBS) containing 1 mM $MgCl_2$ and 20 mM glucose (PBSMG). After washing the cells, the cell pellets were resuspended in PBSMG to achieve a final optical density at 600 nm of 0.6. The bacterial suspension (200 μL) was added to wells of a black, flat-bottom 96-well plate containing test EPI compounds at a concentration of 25 μg/mL or an equivalent volume of the vehicle (DMSO) alone. The final concentration of DMSO in all wells was maintained at 0.25%. A plate vortexer was used to mix the bacterial cells with the test EPI compounds, and the plates are pre-incubated at 37° C. for 5 minutes. After the pre-incubation, 10 μL of Hoechst 33342 was rapidly added to each well such that the final concentration of the fluorescent dye was 10 μM. A SpectraMax® 2 fluorescent plate reader (Molecular Devices, Inc., Sunnyvale, Calif.) was used to monitor the fluorescence of each well at 37° C. once per minute for 40 minutes. The excitation and emission wavelengths were set at 355 and 460 nm, respectively. *E. coli* W4573 and *P. aeruginosa* ATCC 27853 were used as model Gram-negative bacterial strains in this assay. The efflux pump mutant *E. coli* strain N43 (acrA1) was used as a positive control.

TABLE 1
| Example | Structure | Dose (uM/ug ml) | Enhancement |
|---|---|---|---|
| 1 | 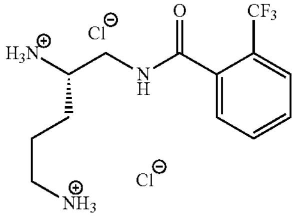 Chemical Formula: $C_{13}H_{20}Cl_2F_3N_3O$ Molecular Weight: 362.22 | 34.5 μM/12.5 | 1 |
| 2 | 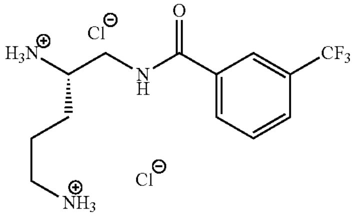 Chemical Formula: $C_{13}H_{20}Cl_2F_3N_3O$ Molecular Weight: 362.22 | 34.5 μM/12.5 | 2 |
| 3 | 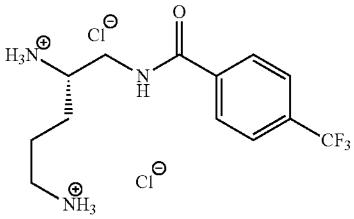 Chemical Formula: $C_{13}H_{20}Cl_2F_3N_3O$ Molecular Weight: 362.22 | 34.5 μM/12.5 | 4 |
| 4 | 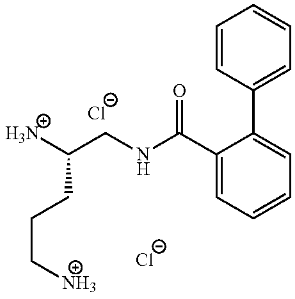 Chemical Formula: $C_{18}H_{25}Cl_2N_3O$ Molecular Weight: 370.32 | 34 μM/12.5 | 2 |
| 5 | 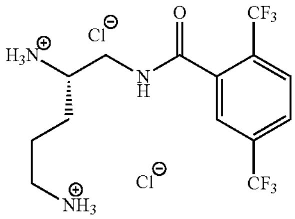 Chemical Formula: $C_{14}H_{19}Cl_2F_6N_3O$ Molecular Weight: 430.22 | 29 μM/12.5 | 2 |

TABLE 1-continued
| Example | Structure | Dose (uM/ug ml) | Enhancement |
|---|---|---|---|
| 6 | 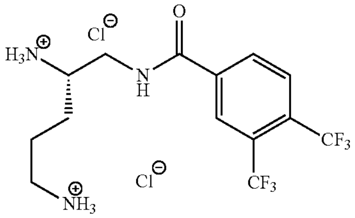 Chemical Formula: $C_{14}H_{19}Cl_2F_6N_3O$ Molecular Weight: 430.22 | 29 µM/12.5 | 32 |
| 7 | 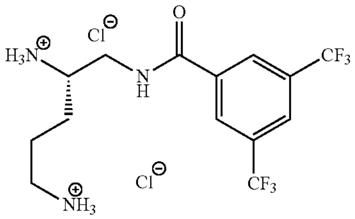 Chemical Formula: $C_{14}H_{19}Cl_2F_6N_3O$ Molecular Weight: 430.22 | 29 µM/12.5 | 16 |
| 8 | 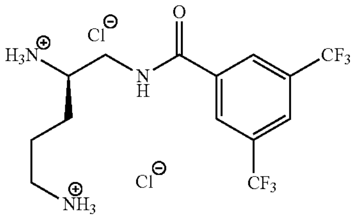 Chemical Formula: $C_{14}H_{19}Cl_2F_6N_3O$ Molecular Weight: 430.22 | 29 µM/12.5 | 8 |
| 9 | 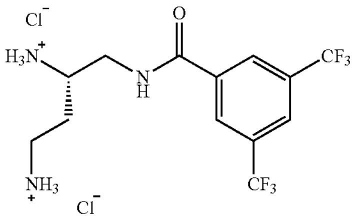 Chemical Formula: $C_{13}H_{17}Cl_2F_6N_3O$ Molecular Weight: 416.19 | 36.4 µM/12.5 | 16 |
| 10 | 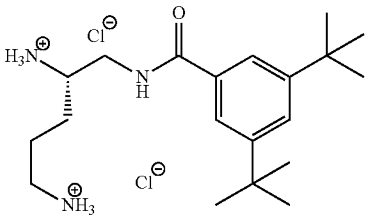 Chemical Formula: $C_{20}H_{37}Cl_2N_3O$ Molecular Weight: 406.44 | 31 µM/12.5 | 64 |

TABLE 1-continued

| Example | Structure | Dose (uM/ug ml) | Enhancement |
|---|---|---|---|
| 11 | 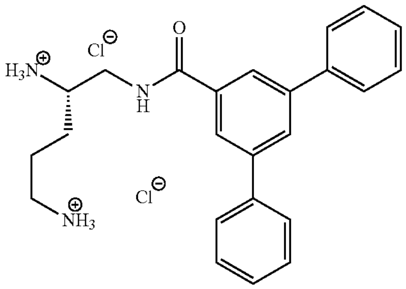 Chemical Formula: $C_{24}H_{29}Cl_2N_3O$ Molecular Weight: 445.41 | 34 μM/12.5 | 128 |
| 12 | 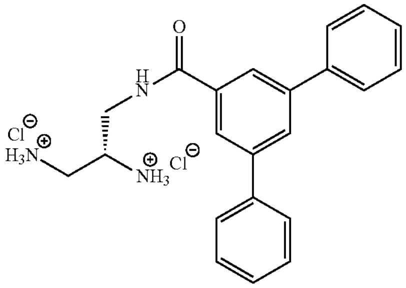 Chemical Formula: $C_{24}H_{29}Cl_2N_3O$ Molecular Weight: 446.42 | 28 μM/12.5 | 2 |
| 13 | 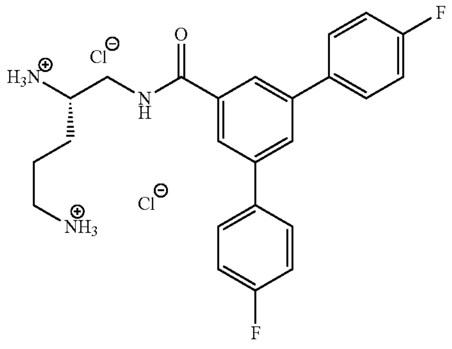 Chemical Formula: $C_{24}H_{27}Cl_2F_2N_3O$ Molecular Weight: 482.39 | 30.5 μM/12.5 | 128 |

The invention will now be illustrated by the following non-limiting examples.

EXAMPLE 1

Preparation of (S)-5-(2-(trifluoromethyl)benzamido)pentane-1,4-diaminium chloride

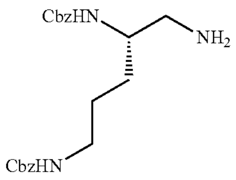

+

-continued

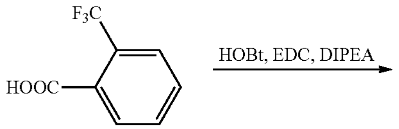

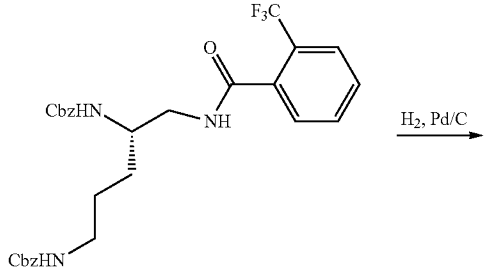

-continued

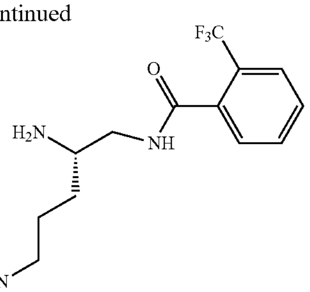

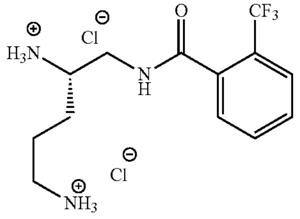

(S)-5-(2-(Trifluoromethyl)benzamido)pentane-1,4-diaminium chloride

A suspension of dibenzyl (5-(2-(trifluoromethyl)benzamido)pentane-1,4-diyl)(S)-dicarbamate (90 mg, 0.16 mmol), 10% Pd/C (20 mg) in methanol (15 mL) was purged and stirred under a hydrogen atmosphere for overnight. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (53 mg, 91% yield). $^{1}H$ NMR (300 MHz, DMSO-d6) δ 8.85 (m, 1H), 8.36 (bs, 3H), 8.08 (bs, 3H), 7.84-7.70 (m, 4H), 3.50 (m, 2H), 3.30 (m, 1H), 2.81 (m, 2H), 1.71 (m, 4H).

The requisite intermediate was prepared as follows

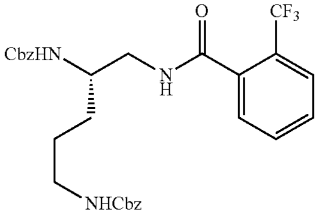

Dibenzyl (5-(2-(trifluoromethyl)benzamido)pentane-1,4-diyl)(S)-dicarbamate

2-Trifluoromethylbenzoic acid (59.1 mg, 0.31 mmol) was dissolved in dry DMF (1.0 mL) and DIPEA (90 μL, 0.58 mmol), HOBt (21.1 mg, 0.16 mmol), EDC (64.5 mg, 0.34 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (113 mg, 78% yield). $^{1}H$ NMR ($CDCl_3$) (300 MHz) δ 7.69 (m, 1H), 7.52 (m, 2H), 7.42 (m, 1H), 7.31 (m, 10H), 5.07 (s, 4H), 3.79 (m, 1H), 3.52-3.41 (m, 2H), 3.20 (m, 2H), 2.25 (m, 4H).

Preparation of Intermediate A (dibenzyl (5-aminopentane-1,4-diyl)(S)-dicarbamate)

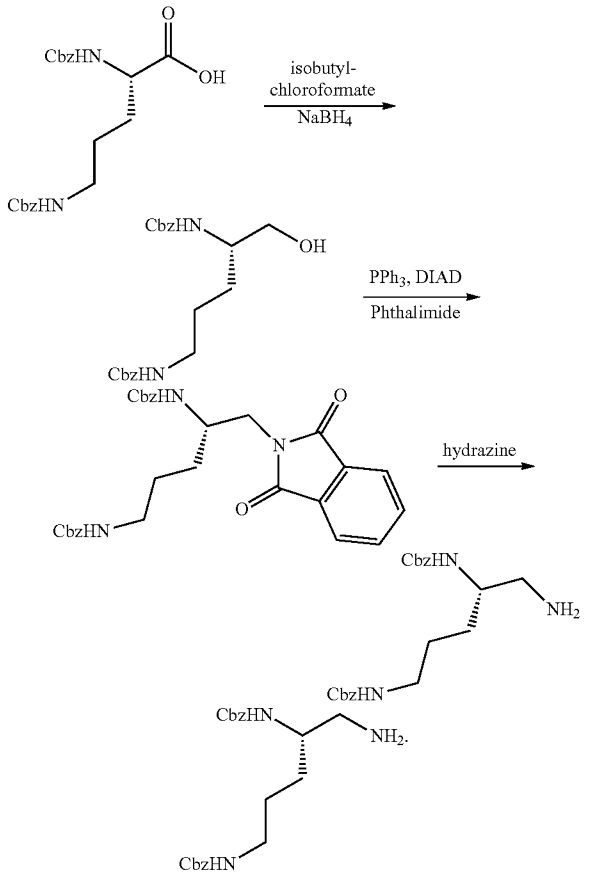

Dibenzyl (5-aminopentane-1,4-diyl)(S)-dicarbamate

Dibenzyl (5-(1,3-dioxoisoindolin-2-yl)pentane-1,4-diyl)(S)-dicarbamate (400 mg, 0.78 mmol) formed was dissolved in methanol (20 mL) and hydrazine monohydrate (80 μL, 1.55 mmol) was added. The reaction mixture was then refluxed for 2 hours and cooled to room temperature. The precipitate formed was filtered and methanol used to wash the filtrate. The filtrate was concentrated under reduced pressure and the remaining solid purified using an ISCO chromatograph with silica (0-10% methanol/methylene chloride+1% $NH_4OH$) to give product as a white powder. (206 mg, 68%); $^{1}H$ NMR ($CDCl_3$) (400 MHz) δ 7.36 (m, 10H), 5.18 (m, 6H), 3.60 (m, 1H), 3.19 (m, 2H), 2.70 (m, 2H), 1.70 (s, 2H), 1.46 (m, 4H); $^{13}C$ NMR δ 156.6, 136.6, 136.5, 128.53, 128.51, 128.1, 128.0, 66.6, 66.5, 53.0, 45.6, 40.7, 29.7. 26.5.

The requisite intermediates were prepared as follows.

Step 1)

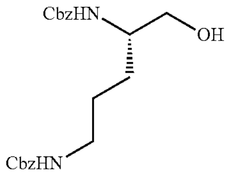

Dibenzyl (5-hydroxypentane-1,4-diyl)(S)-dicarbamate

To a solution of (S)-2,5-bis(((benzyloxy)carbonyl)amino) pentanoic acid (1000 mg, 2.5 mmol) in dimethoxyethane mL) at −15° C. were successively added a solution of N-methyl morpholine (310 μL, 2.82 mmol) and isobutyl chloroformate (320 μL, 2.5 mmol). The reaction was stirred at −15° C. to −10° C. for 15 minutes. The precipitated N-methyl morpholine HCl was removed by filtration and washed with dimethoxyethane (10 mL), the combine filtrates were chilled to −15° C. in an ice-salt bath. Then a solution of sodium borohydride (283 mg, 7.5 mmol) in water (4 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified on column (0-70% ethyl acetate/hexane) to give product as a white powder (508 mg, 52%); $^1H$ NMR ($CDCl_3$) (400 MHz) δ 7.34 (m, 10H), 5.07 (m, 6H), 3.69 (m, 3H), 3.22 (m, 2H), 1.54 (m, 4H); $^{13}C$ NMR δ 156.6, 156.5, 136.5, 136.3, 128.54, 128.52, 128.2, 128.1, 66.8, 66.7, 65.1, 52.8, 40.7, 28.5, 26.5.

Step 2)

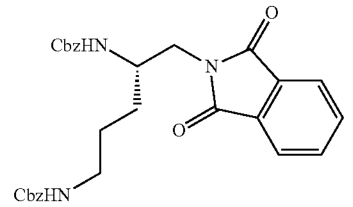

Dibenzyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was concentrated under reduced pressure and residue purified using an ISCO chromatograph with silica (0-70% ethyl acetate/hexane) to give product as a white solid. (491 mg, 92%); $^1H$ NMR ($CDCl_3$) (400 MHz) δ 7.83 (m, 2H), 7.72 (m, 2H), 7.32 (m, 10H), 5.10 (m, 3H), 4.97 (m, 3H), 4.03 (m, 1H) 3.76 (m, 2H), 3.24 (m, 2H), 1.57 (m, 4H); $^{13}C$ NMR δ 168.5, 156.4, 156.2, 136.6, 136.5, 134.0, 132.1, 123.0, 131.9, 131.8, 128.6, 128.5, 128.4, 128.3, 128.0, 127.9, 127.8, 123.4, 66.6, 66.5, 50.7, 41.7, 40.6, 30.0, 26.3.

EXAMPLE 2

Preparation of (S)-5-(3-(trifluoromethyl)benzamido) pentane-1,4-diaminium chloride

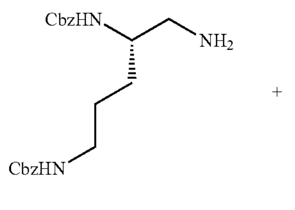

-continued

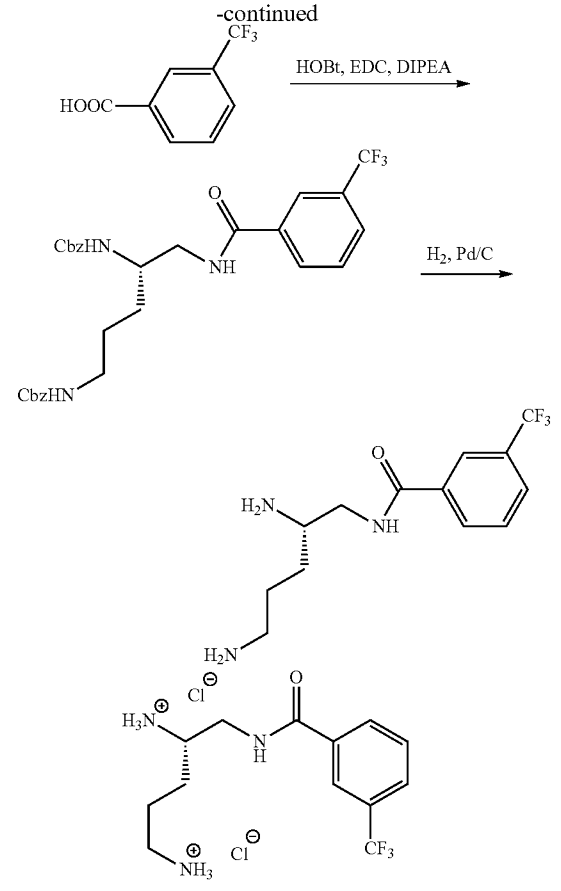

(S)-5-(3-(Trifluoromethyl)benzamido)pentane-1,4-diaminium chloride

A suspension of dibenzyl (5-(3-(trifluoromethyl)benzamido)pentane-1,4-diyl)(S)-dicarbamate (85 mg, 0.15 mmol), 10% Pd/C (20 mg) in methanol (15 mL) was purged and stirred under a hydrogen atmosphere overnight. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (49 mg, 89% yield). $^1H$ NMR (300 MHz, DMSO-$d_6$) δ 9.09 (m, 1H), 8.28 (m, 2H), 8.16 (m, 2H), 7.96 (m, 4H), 7.77 (m, 1H), 3.55 (m, 2H), 3.42 (m, 1H), 2.84 (m, 2H), 1.69 (m, 4H).

The requisite intermediate was prepared as follows.

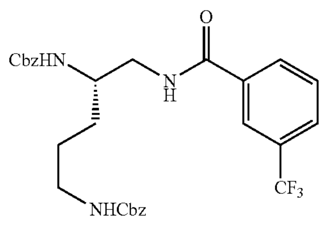

Dibenzyl (5-(3-(trifluoromethyl)benzamido)pentane-1,4-diyl)(S)-dicarbamate

3-Trifluoromethylbenzoic acid (59.1 mg, 0.31 mmol) was dissolved in dry DMF (1.0 mL) and DIPEA (90 μL, 0.58 mmol), HOBt (21.1 mg, 0.16 mmol), EDC (64.5 mg, 0.34 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (103 mg, 70% yield). $^1$H NMR ($CDCl_3$) (300 MHz) δ 7.95 (d, J=6.0 Hz, 1H), 7.77 (d, J=6.0 Hz, 1H), 7.55 (t, 1H), 7.33 (m, 11H), 5.23 (m, 1H), 5.11 (s, 4H), 4.92 (m, 1H), 3.92 (m, 1H), 3.55 (m, 2H), 3.27 (m, 2H), 1.65 (m, 4H).

EXAMPLE 3

Preparation of (S)-5-(4-(trifluoromethyl)benzamido)pentane-1,4-diaminium chloride

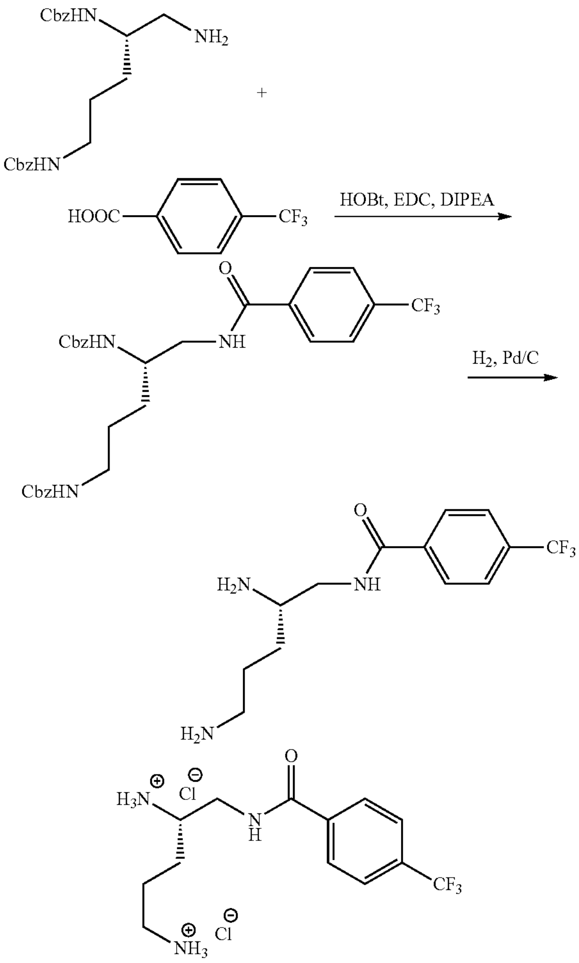

(S)-5-(4-(Trifluoromethyl)benzamido)pentane-1,4-diaminium chloride

A suspension of dibenzyl (5-(4-(trifluoromethyl)benzamido)pentane-1,4-diyl)(S)-dicarbamate (80 mg, 0.14 mmol), 10% Pd/C (20 mg) in methanol (15 mL) was purged and stirred under a hydrogen atmosphere overnight. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (41 mg, 79% yield). $^1$H NMR (300 MHz, DMSO-$d_6$) δ 9.09 (m, 1H), 8.17 (m, 4H), 7.92 (m, 4H), 3.55 (m, 2H), 2.83 (m, 2H), 1.78 (m, 4H).

The requisite intermediate was prepared as follows:

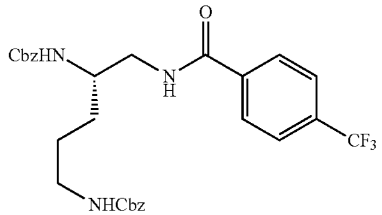

Dibenzyl (5-(4-(trifluoromethyl)benzamido)pentane-1,4-diyl)(S)-dicarbamate

4-Trifluoromethylbenzoic acid (59.1 mg, 0.31 mmol) was dissolved in dry DMF (1.0 mL) and DIPEA (90 μL, 0.58 mmol), HOBt (21.1 mg, 0.156 mmol), EDC (64.5 mg, 0.34 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (107 mg, 72% yield). $^1$H NMR (300 MHz, $CDCl_3$) δ 7.89 (m, 2H), 7.69 (m, 2H), 7.31 (m, 10H), 5.11 (m, 4H), 3.92 (m, 1H), 3.65 (m, 2H), 3.46-3.39 (m, 1H), 3.24-3.18 (m, 1H), 1.84 (m, 2H).

EXAMPLE 4

Preparation of (S)-5-([1,1'-biphenyl]-2-carboxamido)pentane-1,4-diaminium chloride

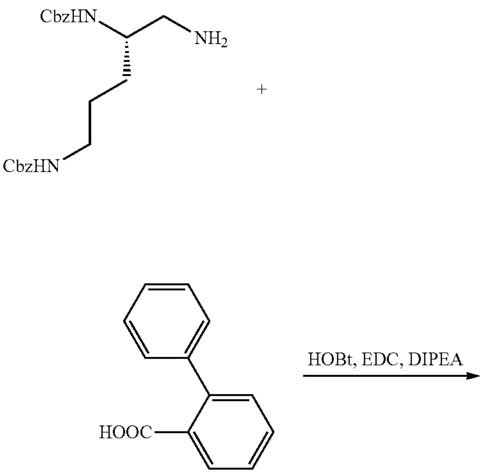

-continued

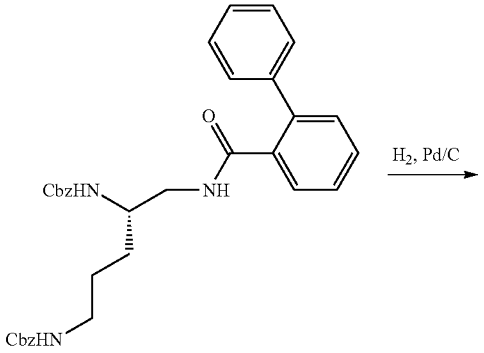

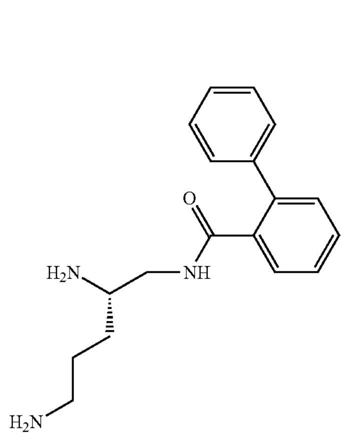

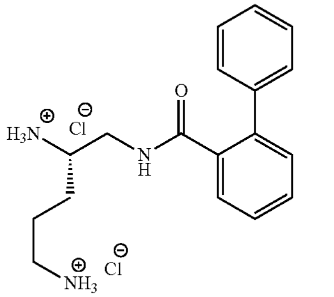

(S)-5-([1,1′-Biphenyl]-2-carboxamido)pentane-1,4-diaminium chloride

A suspension of dibenzyl (5-([1,1'-biphenyl]-2-carboxamido)pentane-1,4-diyl)(S)-dicarbamate (95 mg, 0.16 mmol), 10% Pd/C (20 mg) in methanol (15 mL) was purged and stirred under a hydrogen atmosphere for overnight. After all starting material was consumed; the catalyst was filtered through Celite. The filtrate was added with 0.5 mL of 4N HCl in dioxane and was stirred at room temperature for 10 minutes. The solvent was removed to give a residue which was then triturated with ethyl acetate to afford the pure product as white solid (52 mg, 81% yield). $^{1}H$ NMR (300 MHz, DMSO-d6) δ 8.44 (m, 1H), 8.19 (m, 2H), 8.01 (m, 2H), 7.41 (m, 9H), 3.35 (m, 2H), 3.15 (m, 1H), 2.7 (m, 2H), 1.5 (m, 4H).

The requisite intermediate was prepared as follows:

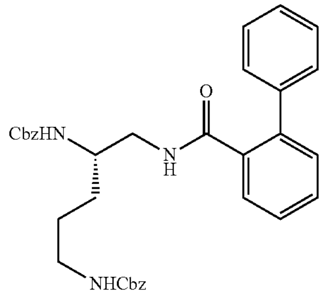

Dibenzyl (5-([1,1′-biphenyl]-2-carboxamido)pentane-1,4-diyl)(S)-dicarbamate

2-Carboxy[1,1']biphenyl (67.3 mg, 0.34 mmol) was dissolved in dry DMF (1.0 mL) and DIPEA (90 μL, 0.58 mmol), HOBt (23.4 mg, 0.16 mmol), EDC (65.2 mg, 0.34 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (120 mg, 83% yield). NMR ($CDCl_3$) (300 MHz) δ 7.67 (m, 2H), 7.52 (m, 2H), 7.35 (m, 15H), 5.55 (m, 1H), 5.09 (s, 2H), 5.06 (s, 2H), 4.90 (m, 1H), 4.65 (m, 1H), 3.47 (m, 1H), 3.24 (m, 4H), 1.47 (m, 3H), 1.20 (m, 2H).

EXAMPLE 5

Preparation of (S)-5-(2,5-bis(trifluoromethyl)benzamido)pentane-1,4-diaminium chloride

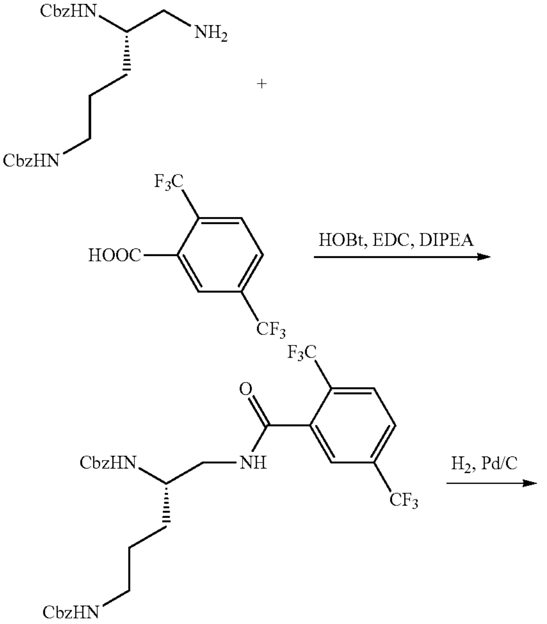

-continued

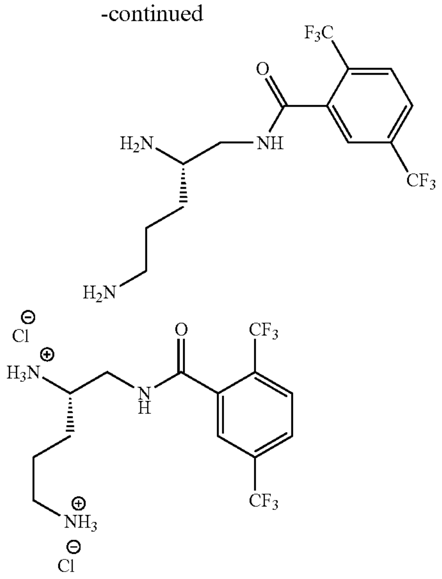

(S)-5-(2,5-Bis(trifluoromethyl)benzamido)pentane-1,4-diaminium chloride

A suspension of dibenzyl (5-(2,5-bis(trifluoromethyl)benzamido)pentane-1,4-diyl)(S)-dicarbamate (100 mg, 0.16 mmol), 10% Pd/C (20 mg) in methanol (15 mL) was purged and stirred overnight under a hydrogen atmosphere. After all starting material was consumed; the catalyst was filtered through Celite. The filtrate was added with 0.5 mL of 4N HCl in dioxane and was stirred at room temperature for 10 minutes. The solvent was removed to give a residue which was then triturated with ethyl acetate to afford the pure product as white solid (53 mg, 77% yield). $^1H$ NMR (300 MHz, DMSO-d6) δ 9.02 (m, 1H), 8.25 (m, 4H), 8.10 (m, 2H), 7.95 (bs, 3H), 3.51 (m, 3H), 2.84 (m, 2H), 1.70 (m, 4H).

The requisite intermediate was prepared as follows:

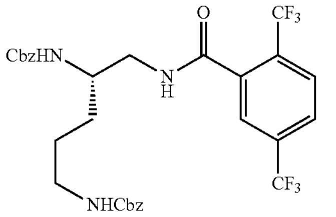

Dibenzyl (5-(2,5-bis(trifluoromethyl)benzamido)pentane-1,4-diyl)(S)-dicarbamate 2,5-Bis(trifluoromethyl)benzoic acid (80.3 mg, 0.31 mmol) was dissolved in dry DMF (1.0 mL) and DIPEA (90 μL, 0.58 mmol), HOBt (21.2 mg, 0.156 mmol), EDC (59.6 mg, 0.31 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (113 mg, 69% yield). $^1H$ NMR ($CDCl_3$) (300 MHz) δ 7.82 (m, 3H), 7.30 (m, 10H), 5.05 (s, 4H), 4.87 (m, 1H), 3.88 (m, 1H), 3.55 (m, 2H), 3.24 (m, 2H), 1.63 (m, 4H).

EXAMPLE 6

Preparation of (S)-5-(3,4-Bis(trifluoromethyl)benzamido)pentane-1,4-diaminium chloride

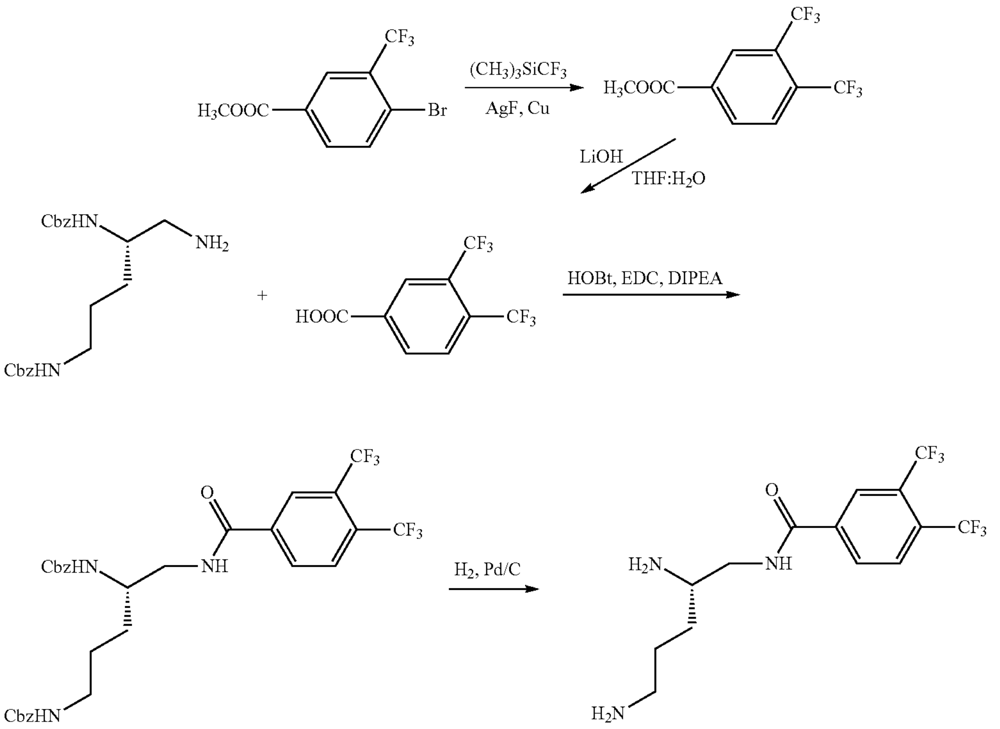

-continued

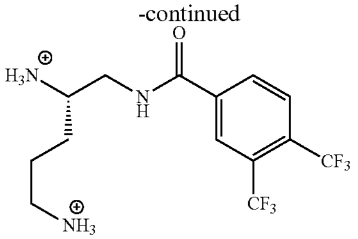

(S)-5-(3,4-Bis(trifluoromethyl)benzamido)pentane-1,4-diaminium

A suspension of dibenzyl (5-(3,4-bis(trifluoromethyl)benzamido)pentane-1,4-diyl)(S)-dicarbamate (100 mg, 0.16 mmol), 10% Pd/C (20 mg) in methanol (15 mL) was purged and stirred under a hydrogen atmosphere for overnight. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (44 mg, 64% yield). $^{1}H$ NMR (300 MHz, DMSO-d6) δ 9.54 (m, 1H), 8.65 (s, 1H), 8.60 (d, J=9.0 Hz, 1H), 8.38 (m, 4H), 8.15 (m, 3H), 3.67 (m, 3H), 2.92 (m, 2H), 1.82 (m, 4H).

The requisite intermediates were prepared as follows:

a.

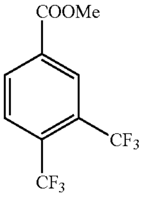

Methyl bis(3,4-(trifluoromethyl)benzoate

To a well stirred mixture of AgF (1.27 g, 10 mmol) in 10 mL of DMF, $Me_3SiCF_3$ (1.7 g, 12 mmol) was added at room temperature. The mixture was stirred for 30 minutes and copper powder (1.0 g, 15 mmol) was added. After stirring for 4 hours, the formation of $CuCF_3$ was complete. Commercially available methyl 4-bromo-3-(trifluoromethyl)benzoate (1.27 g, 4.5 mmol) was added and the reaction mixture was heated at 100° C. overnight. The mixture was filtered from the solid precipitate and poured into 50 mL of water. The organic layer was extracted with ethyl acetate and dried over sodium sulfate. The solvent was evaporated and the crude product was purified using ISCO to give the desired compound as colorless oil (820 mg, 73% yield). $^{1}H$ NMR ($CDCl_3$) (300 MHz) δ 8.55 (s, 1H), 8.37 (d, J=9.0 Hz, 1H), 7.99 (d, J=9.0 Hz, 1H), 4.09 (s, 3H).

b.

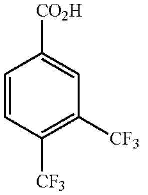

Bis(3,4-(trifluoromethyl)benzoic acid

To a solution of methyl 3,4-bis(trifluoromethyl)benzoate (400 mg, 1.47 mmol) in THF: $H_2O$ (6 mL:2 mL) was added 100 mg LiOH. The reaction mixture was heated at 65° C. overnight. The solvent was removed and 1N HCl was added. The resulting precipitate was filtered, dried to afford the acid which was pure enough to be used for the next step. $^{1}H$ NMR (300 MHz, DMSO-d6) δ 8.44 (m, 2H), 8.24 (m, 1H).

c.

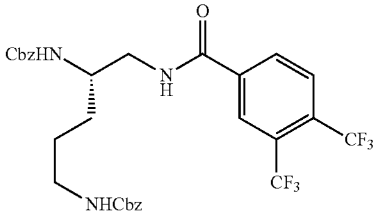

Dibenzyl (5-(3,4-bis(trifluoromethyl)benzamido)pentane-1,4-diyl)(S)-dicarbamate 3,4-Bis(trifluoromethyl)benzoic acid (80.3 mg, 0.31 mmol) was dissolved in dry DMF (1.0 mL) and DIPEA (90 μL, 0.58 mmol), HOBt (21.2 mg, 0.156 mmol), EDC (59.6 mg, 0.31 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (111 mg, 68% yield). LC/MS: 626.3 (M+H).

EXAMPLE 7

Preparation of (S)-5-(3,5-bis(trifluoromethyl)benzamido)pentane-1,4-diaminium chloride

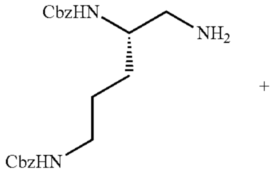

-continued

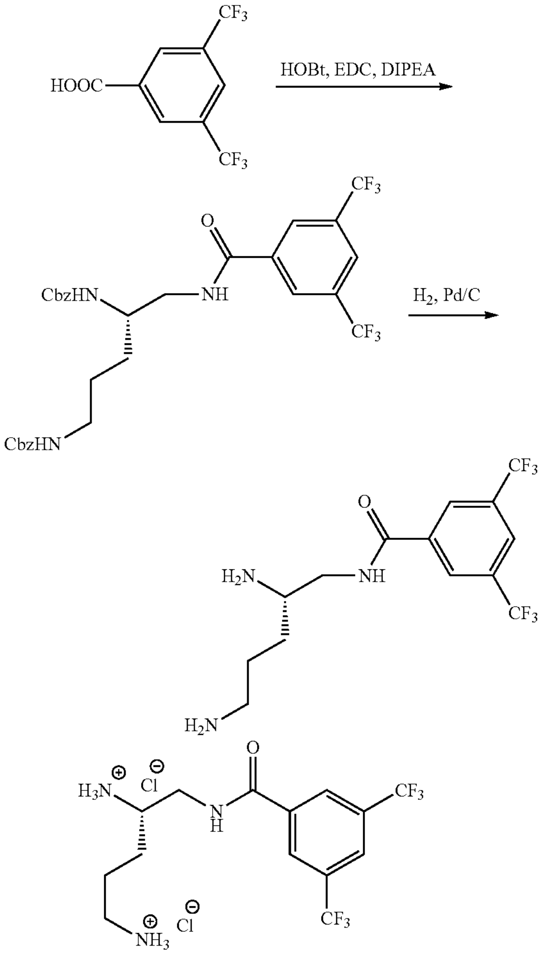

(S)-5-(3,5-Bis(trifluoromethyl)benzamido)pentane-1,4-diaminium chloride

A suspension of dibenzyl (5-(3,5-bis(trifluoromethyl)benzamido)pentane-1,4-diyl)(S)-dicarbamate (95 mg, 0.15 mmol), 10% Pd/C (20 mg) in methanol (15 mL) was purged and stirred overnight under a hydrogen atmosphere. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (55 mg, 85% yield). $^1$H NMR (300 MHz, DMSO-d6) δ 9.14 (m, 2H), 8.58 (m, 4H), 8.34 (m, 2H), 3.25 (m, 3H), 2.90 (m, 2H), 1.78 (m, 4H).

The requisite intermediate was prepared as follows:

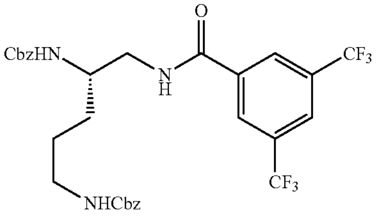

Dibenzyl (5-(3,5-bis(trifluoromethyl)benzamido)pentane-1,4-diyl)(S)-dicarbamate 3,5-Bis(trifluoromethyl)benzoic acid (80.3 mg, 0.31 mmol) was dissolved in dry DMF (1.0 mL) and DIPEA (90 μL, 0.58 mmol), HOBt (21.2 mg, 0.16 mmol), EDC (59.6 mg, 0.31 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (119 mg, 73% yield). $^1$H NMR (300 MHz, $CDCl_3$) δ 8.32 (s, 2H), 8.04 (s, 1H), 7.60 (bs, 1H), 7.31 (m, 10H), 5.5 (bs, 1H), 5.28 (bs, 1H), 5.11 (m, 4H), 3.92 (m, 1H), 3.65 (m, 2H), 3.46-3.39 (m, 1H), 3.24-3.18 (m, 1H), 1.84 (m, 2H).

EXAMPLE 8

Preparation of (R)-5-(3,5-bis(trifluoromethyl)benzamido)pentane-1,4-diaminium chloride

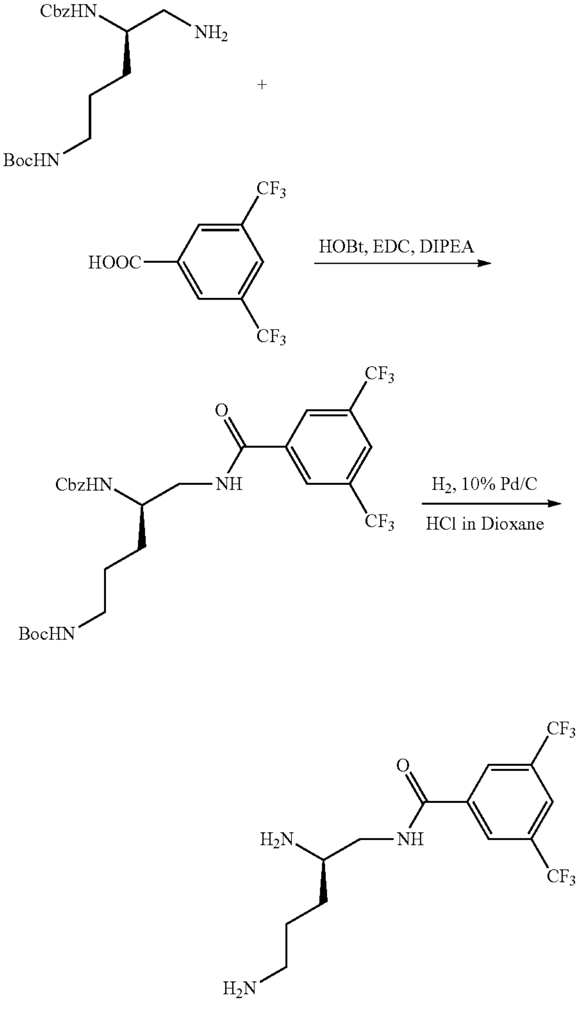

-continued

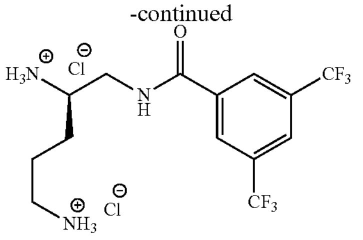

(R)-5-(3,5-Bis(trifluoromethyl)benzamido)pentane-1,4-diaminium chloride

A suspension of benzyl t-butyl (5-(3,5-bis(trifluoromethyl)benzamido)pentane 1,4-diyl (R)-dicarbamate (95 mg, 0.15 mmol), 10% Pd/C (20 mg) in methanol (15 mL) was purged and stirred overnight under a hydrogen atmosphere. After all starting material was consumed; the catalyst was filtered through Celite. The filtrate was added with 1.0 mL of 4N HCl in dioxane and was stirred at room temperature for 90 minutes. The solvent was removed to give a residue which was then triturated with ethyl acetate to afford the pure product as white solid (58 mg, 85% yield). $^{1}H$ NMR (300 MHz, DMSO-d6) δ 9.84 (bs, 1H), 9.02 (bs, 2H), 8.73 (bs, 4H), 8.46 (bs, 3H), 397 (m, 3H), 3.21 (m, 2H), 2.12 (m, 4H).

Preparation of Intermediate B (benzyl t-butyl (5-aminopentane-1,4-diyl)(R)-dicarbamate)

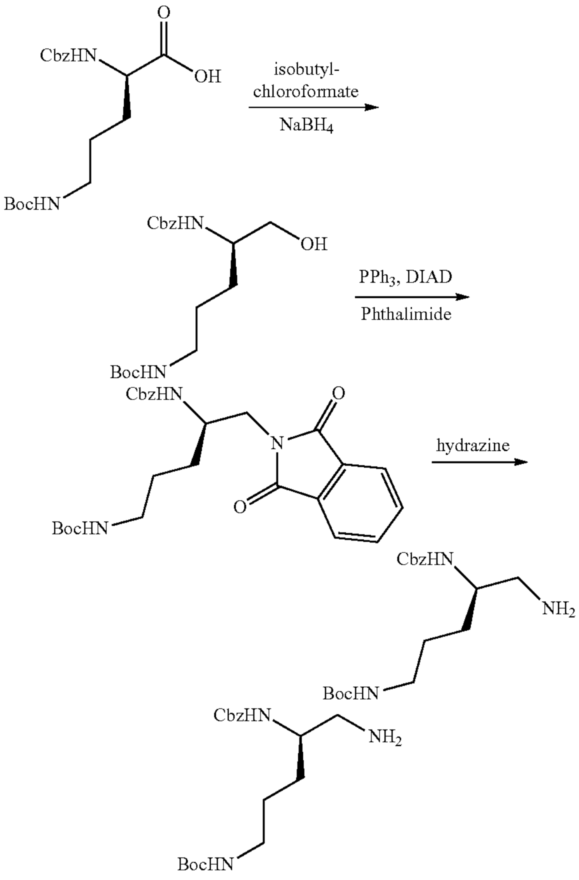

Benzyl t-butyl (5-aminopentane-1,4-diyl)(R)-dicarbamate

Benzyl t-butyl (5-(1,3-dioxoisoindolin-2-yl)pentane-1,4-diyl)(R)-dicarbamate (700 mg, 1.45 mmol) formed was dissolved in methanol (15 mL) and hydrazine monohydrate (0.14 mL, 2.90 mmol) was added. The reaction mixture was then refluxed for 2 hours and cooled to room temperature. The precipitate formed was filtered and methanol used to wash the filtrate. The filtrate was concentrated under reduced pressure and the remaining solid purified using an ISCO chromatograph with silica (0-10% Methanol/methylene chloride+1% $NH_4OH$) to give product as a yellow oil. (166 mg, 33%); 1H NMR ($CDCl_3$) (400 MHz) δ 7.25 (m, 5H), 5.41 (d, 1H, J=8), 5.00 (s, 1H), 4.84 (brs, 1H); 3.50 (m, 1H), 3.01 (m, 2H), 2.61 (m, 2H), 1.40 (m, 4H), 1.36 (s, 9H); $^{13}C$ NMR δ 156.6, 156.0, 136.6, 128.4, 128.1, 128.0, 78.9, 66.6, 53.2, 45.7, 40.2, 29.7, 28.4, 26.6, 25.0, 24.9.

Step 1)

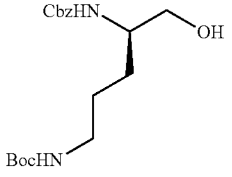

Benzyl t-butyl (5-hydroxypentane-1,4-diyl)(R)-dicarbamate

To a solution of (R)-2-(((benzyloxy)carbonyl)amino)-5-((t-butoxycarbonyl)amino)pentanoic acid (1000 mg, 2.73 mmol) in dimethoxyethane (10 mL) at −15° C. were successively added a solution of N-methyl morpholine (0.34 mL, 3.08 mmol) and isobutyl chloroformate (0.35 mL, 2.73 mmol). The reaction was stirred at −15° C. to −10° C. for 15 minutes. The precipitated N-methyl morpholine HCl was removed by filtration and washed with dimethoxyethane (10 mL), the combine filtrates were chilled to −15° C. in an ice-salt bath. Then a solution of sodium borohydride (310 mg, 8.19 mmol) in water (4 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified on column (0-70% ethyl acetate/hexane) to give product as a colorless oil (855 mg, 91%); 1H NMR ($CDCl_3$) (400 MHz) δ 7.28 (m, 5H), 5.02 (s, 3H), 3.60 (m, 4H), 3.04 (m, 2H), 1.47 (m, 4H), 1.36 (m, 9H); $^{13}C$ NMR δ 156.6, 156.1, 136.4, 128.5, 128.1, 128.0, 79.3, 66.8, 65.0, 62.7, 52.9, 52.4, 40.3, 29.8, 28.4, 26.7, 26.0.

Step 2)

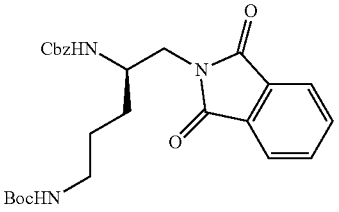

Benzyl t-butyl (5-(1,3-dioxoisoindolin-2-yl)pentane-1,4-diyl)(R)-dicarbamate

Triphenylphosphine (652 mg, 2.49 mmol) and phthalimide (366 mg, 2.49 mmol) were added to a flask containing dry THF (5 mL) Benzyl t-butyl (5-hydroxypentane-1,4-diyl) (R)-dicarbamate (730 mg, 2.27 mmol) was added and the flask was cooled to 0° C. DIAD (503 mg, 2.49 mmol) was added dropwise and reaction was allowed to stir for 30 minutes at 0° C. and overnight at room temperature. The mixture was concentrated under reduced pressure and the residue purified on an ISCO chromatograph with silica (0-70% ethyl acetate/hexane) to give product as a yellow solid. (736 mg, 73%); 1H NMR ($CDCl_3$) (400 MHz) δ 7.82 (m, 2H), 7.71 (m, 2H), 7.27 (m, 5H), 5.18 (brs, 1H), 4.96 (m, 2H), 4.67 (brs, 1H), 4.02 (m, 1H) 3.75 (m, 2H), 3.14 (m, 2H), 1.55 (m, 4H), 1.44 (s, 9H); $^{13}C$ NMR δ 168.4, 156.3, 156.0, 136.6, 133.9, 131.8, 128.4, 128.3, 127.8, 127.7, 123.3, 78.9, 66.3, 60.3, 50.7, 41.9, 40.2, 29.9, 28.4, 26.4.

Step 3)

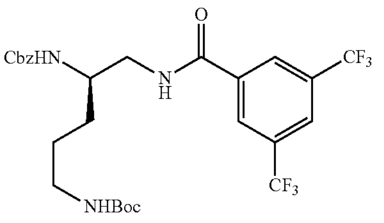

Benzyl tert-butyl (5-(3,5-bis(trifluoromethyl)benzamido)pentane-1,4-diyl)(R)-dicarbamate 3,5-Bis(trifluoromethyl)benzoic acid (80.3 mg, 0.31 mmol) was dissolved in dry DMF (1.0 mL) and DIPEA (92.1 μL, 0.71 mmol), HOBt (23.1 mg, 0.17 mmol), EDC (65.6 mg, 0.39 mmol) were added. The reaction mixture was stirred at room temperature for 5 minutes. Benzyl tert-butyl (5-aminopentane-1,4-diyl)(R)-dicarbamate (Intermediate B) (100 mg, 0.29 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (109 mg, 65% yield). 1H NMR ($CDCl_3$) (300 MHz) δ 8.27 (m, 4H), 7.98 (m, 2H), 7.39 (m, 2H), 4.71 (s, 2H), 3.58 (m, 2H), 2.95 (m, 2H), 1.59 (m, 13H).

EXAMPLE 9

Preparation of (S)-4-(3,5-bis(trifluoromethyl)benzamido)butane-1,3-diaminium chloride

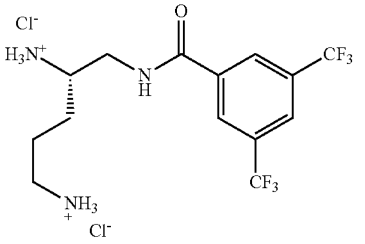

(S)-4-(3,5-bis(trifluoromethyl)benzamido)butane-1,3-diaminium chloride

A suspension of dibenzyl (4-(3,5-bis(trifluoromethyl)benzamido)butane-1,3-diyl)(S)-dicarbamate (90 mg, 0.15 mmol), 10% Pd/C (20 mg) in methanol (15 mL) was purged and stirred overnight under a hydrogen atmosphere. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (52 mg, 85% yield). $^1H$ NMR (300 MHz, DMSO-d6) δ 9.46 (m, 1H), 8.63 (s, 2H), 8.38 (m, 4H), 8.08 (m, 4H), 3.62-3.51 (m, 5H), 3.04 (m, 2H), 1.96 (m, 2H).

Preparation of Intermediate C (dibenzyl (4-aminobutane-1,3-diyl)(S)-dicarbamate)

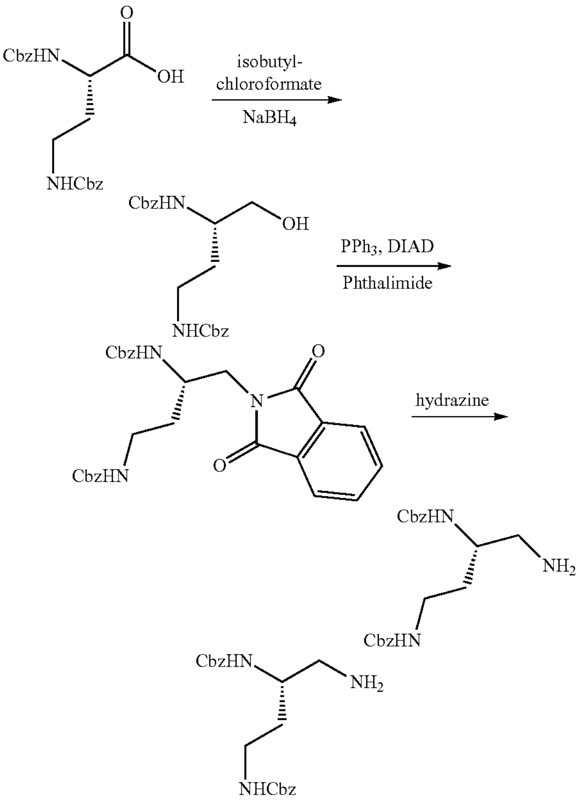

Dibenzyl (4-aminobutane-1,3-diyl)(S)-dicarbamate

Dibenzyl (4-(1,3-dioxoisoindolin-2-yl)butane-1,3-diyl) (S)-dicarbamate (170 mg, 0.34 mmol) was dissolved in methanol (5 mL) and hydrazine monohydrate (0.03 mL, 0.68 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO chromatograph with silica (0-10% methanol/methylene chloride+1% $NH_4OH$) to give product as a white powder. (77 mg, 61%); $^1H$ NMR ($CDCl_3$) (400 MHz) δ 7.34 (m, 10H), 5.77 (brs, 1H), 5.56 (d, 1H, J=8), 5.09 (m, 4H), 3.69 (m, 1H), 3.44 (m, 1H), 3.02 (m, 1H), 2.74 (m, 2H), 2.26 (s, 2H), 1.68 (m, 1H), 1.47 (m, 1H); $^{13}C$ NMR 157.0, 156.5, 136.7, 136.4, 128.5, 128.4, 128.1, 128.0, 66.8, 66.5, 50.5, 45.5, 37.6, 33.0.

The requisite intermediate was prepared as follows:

Step 1)

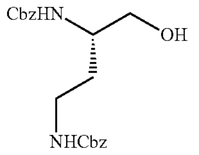

Dibenzyl (4-hydroxybutane-1,3-diyl)(S)-dicarbamate

To a solution of (S)-2,4-bis(((benzyloxy)carbonyl)amino) butanoic acid (1000 mg, 2.77 mmol) in dimethoxymethane (10 mL) at −15° C. were successively added N-methyl morpholine (340 μL, 3.13 mmol) and isobutyl chloroformate (360 μL, 2.77 mmol). The reaction was stirred at −15° C. to −10° C. for 15 minutes. The precipitated N-methyl morpholine HCl was removed by filtration and washed with dimethoxyethane (10 mL) and the combine filtrates were chilled to −15° C. in an ice-salt bath. Then a solution of sodium borohydride (378 mg, 8.31 mmol) in water (5 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified on column (0-70% ethyl acetate/hexane) to give product as a white powder (491 mg, 48%); $^1H$ NMR ($CDCl_3$) (400 MHz) 7.33 (m, 10H), 5.72 (s, 1H), 5.63 (d, 1H, J=8), 5.08 (s, 4H), 3.48 (m, 5H), 3.02 (m, 1H), 1.71 (m, 1H), 1.57 (m, 1H); $^{13}C$ NMR 157.0, 156.7, 136.5, 136.3, 128.55, 128.50, 128.1, 128.07, 128.02, 66.8, 66.6, 64.6, 50.4, 37.7, 31.7.

Step 2)

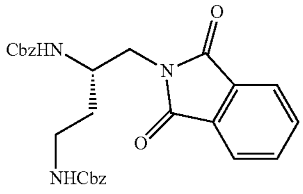

Dibenzyl (4-(1,3-dioxoisoindolin-2-yl)butane-1,3-diyl)(S)-dicarbamate

Triphenylphosphine (365 mg, 1.39 mmol) and phthalimide (204 mg, 1.39 mmol) were added to a flask containing dry THF (6 mL). Dibenzyl (4-hydroxybutane-1,3-diyl)(S)-dicarbamate (432 mg, 1.39 mmol) was added and the flask was cooled to 0° C. DIAD (281 mg, 1.39 mmol) was added dropwise and reaction allowed to stir for 30 minutes at 0° C. and overnight at room temperature. The mixture was concentrated under reduced pressure and residue purified on an ISCO chromatograph with silica (0-70% ethyl acetate/hexane) to give the product as a white solid. (237 mg, 41%); $^1H$ NMR ($CDCl_3$) (400 MHz) δ 7.83 (m, 2H), 7.70 (m, 2H), 7.36 (m, 10H), 5.61 (brs, 1H), 5.46 (d, 1H, J=8), 5.10 (m, 4H), 4.12 (m, 1H), 3.78 (m, 2H), 3.51 (m, 1H), 3.08 (m, 1H), 1.83 (m, 1H), 1.54 (m, 1H); $^{13}C$ NMR 168.5, 156.7, 156.5, 136.7, 136.4, 134.1, 131.7, 128.46, 128.41, 128.0, 127.9, 127.7, 123.4, 66.6, 66.5, 53.4, 48.8, 41.8, 37.4, 33.2.

Step 3)

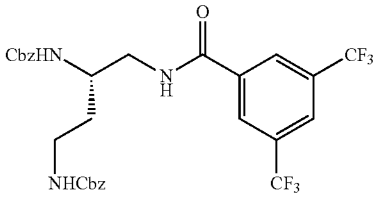

Dibenzyl (4-(3,5-bis(trifluoromethyl)benzamido)butane-1,3-diyl)(S)-dicarbamate 3,5-Bis(trifluoromethyl)benzoic acid (80.8 mg, 0.313 mmol) was dissolved in dry DMF (1.0 mL) and DIPEA (123.64, 0.71 mmol), HOBt (23.1 mg, 0.171 mmol), EDC (65.6 mg, 0.34 mmol) were added. The reaction mixture was stirred at room temperature for 5 minutes. Dibenzyl (4-aminobutane-1,3-diyl)(S)-dicarbamate (Intermediate C) (100 mg, 0.27 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (105 mg, 64% yield). $^1H$ NMR ($CDCl_3$) (300 MHz) δ 8.33 (s, 2H), 8.04 (s, 1H), 7.60 (bs, 1H), 7.31 (m, 10H), 5.49 (m, 1H), 5.28 (m, 1H), 5.13 (s, 2H), 5.11 (s, 2H), 3.93 (m, 1H), 3.65 (m, 2H), 3.46-3.39 (m, 1H), 3.21 (m, 1H), 1.84 (m, 2H).

EXAMPLE 10

Preparation of (S)-5-(3,5-di-tert-butylbenzamido) pentane-1,4-diaminium chloride

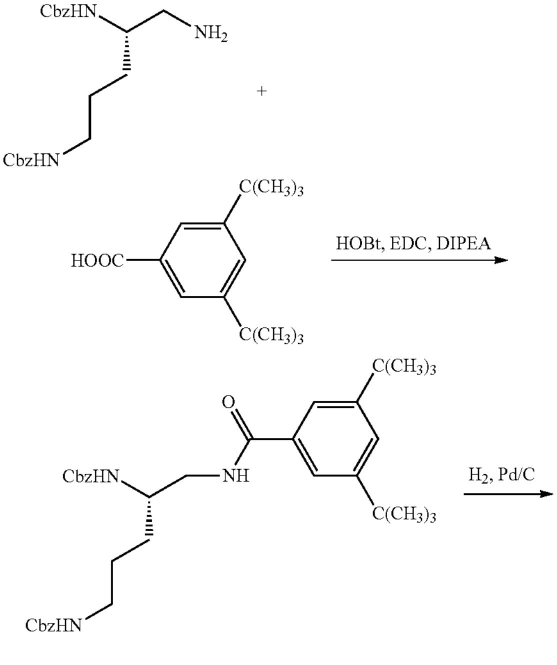

-continued

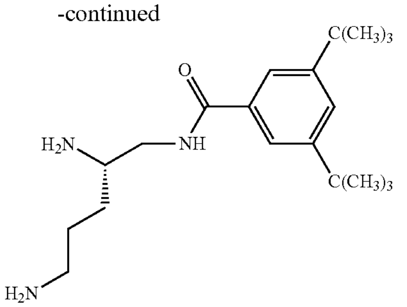

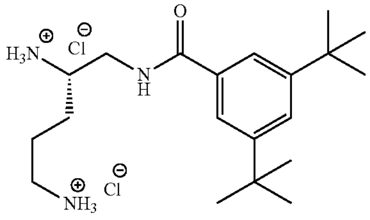

(S)-5-(3,5-Di-tert-butylbenzamido)pentane-1,4-diaminium chloride

A suspension of dibenzyl (5-(3,5-di-t-butylbenzamido) pentane-1,4-diyl)(S)-dicarbamate (95 mg, 0.16 mmol), 10% Pd/C (20 mg) in methanol (15 mL) was purged and stirred under a hydrogen atmosphere for overnight. After all starting material was consumed; the catalyst was filtered through Celite. The filtrate was added with 0.5 mL of 4N HCl in dioxane and was stirred at room temperature for 10 minutes. The solvent was removed to give a residue which was then triturated with ethyl acetate to afford the pure product as white solid (52 mg, 81% yield). $^1$H NMR (300 MHz, DMSO-d6) δ 8.96 (m, 1H), 8.11 (bs, 5H), 7.83 (s, 2H), 7.56 (s, 1H), 3.55 (m, 3H), 2.83 (m, 2H), 1.72 (m, 4H), 1.34 (s, 18H).

The requisite intermediate was prepared as follows:

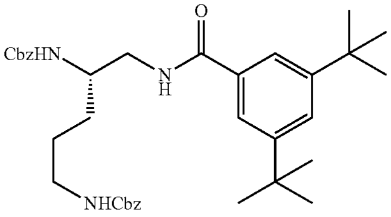

Dibenzyl (5-(3,5-di-tert-butylbenzamido)pentane-1,4-diyl)(S)-dicarbamate 3,4-Bis(t-butyl)benzoic acid (72.9 mg, 0.31 mmol) was dissolved in dry DMF (1.0 mL) and DIPEA (90 μL, 0.58 mmol), HOBt (21.1 mg, 0.16 mmol), EDC (59.6 mg, 0.31 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (115 mg, 74% yield). $^1$H NMR ($CDCl_3$) (300 MHz) δ 7.67 (m, 2H), 7.59 (s, 1H), 7.34 (m, 5H), 7.29 (m, 5H), 7.14 (m, 1H), 5.38 (m, 1H), 5.09 (s, 4H), 5.02 (m, 1H), 3.87 (m, 1H), 3.53 (m, 2H), 3.22 (m, 2H), 1.57 (m, 4H), 1.36 (s, 18H).

EXAMPLE 11

Preparation of (S)-5-([1,1':3',1"-terphenyl]-5'-carboxamido)pentane-1,4-diaminium chloride

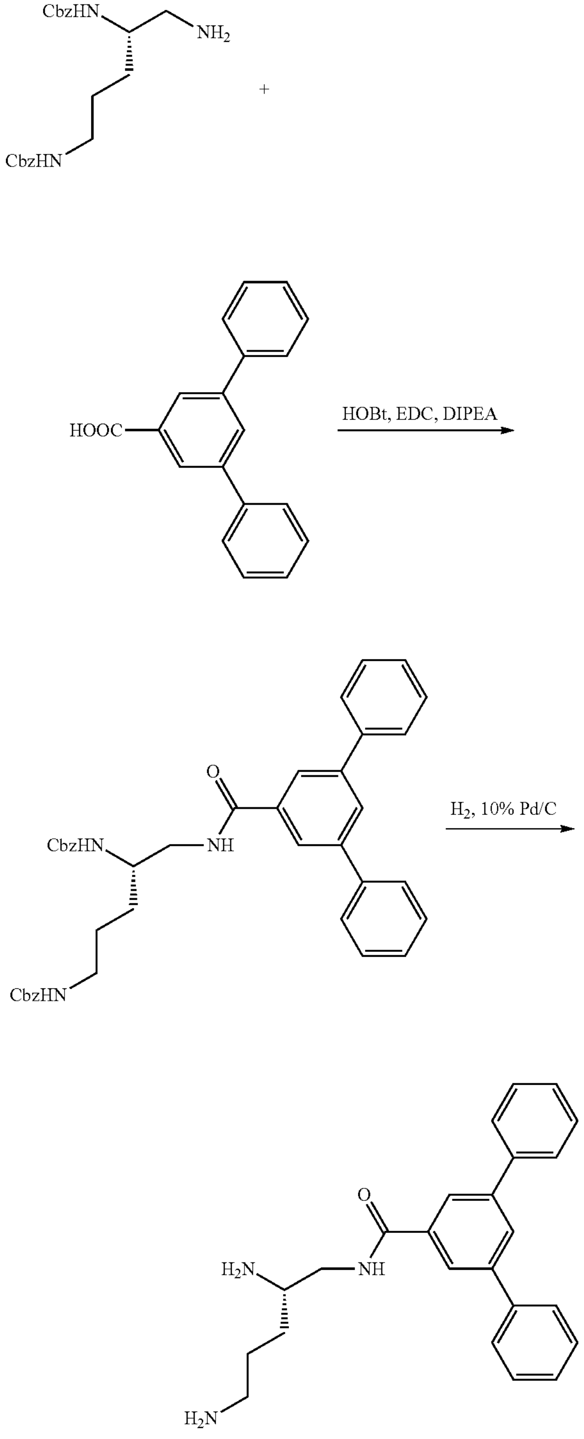

-continued

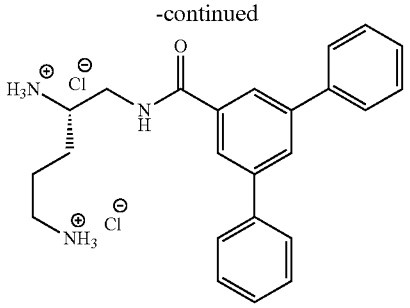

(S)-5-([1,1′:3′,1″-Terphenyl]-5′-carboxamido)pentane-1,4-diaminium chloride

A suspension of dibenzyl (5-([1,1':3',1"-terphenyl]-5'-carboxamido)pentane-1,4-diyl)(S)-dicarbamate (100 mg, 0.16 mmol), 10% Pd/C (20 mg) in methanol (15 mL) was purged and stirred under a hydrogen atmosphere for overnight. After all of the starting material was consumed, the catalyst was filtered through Celite. The filtrate was added with 0.5 mL of 4N HCl in dioxane and was stirred at room temperature for 10 minutes. The solvent was removed to give a residue which was then triturated with ethyl acetate to afford the pure product as white solid (50 mg, 72% yield). $^1$H NMR (300 MHz, DMSO-$d_6$) δ 8.94 (bs, 1H), 8.57 (m, 5H), 8.18 (m, 2H), 8.08 (s, 1H), 7.88 (m, 4H), 7.57-7.43 (m, 6H), 3.40 (m, 3H), 3.14 (m, 2H), 1.74 (m, 4H).

The requisite intermediate was prepared as follows:

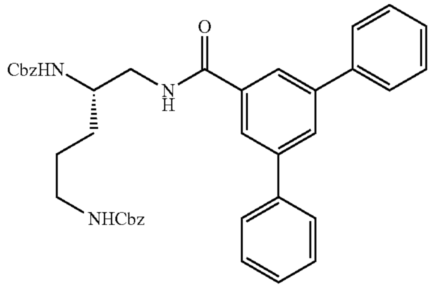

Dibenzyl (5-([1,1′:3′,1″-terphenyl]-5′-carboxamido)pentane-1,4-diyl)(S)-dicarbamate

[1,1':3',1"-Terphenyl]-5'-carboxylic acid (100 mg, 0.37 mmol) was dissolved in dry dichloromethane (5 mL) and oxalyl chloride (48 μL, 0.55 mmol) was added followed by a catalytic amount of DMF (2 drops). The reaction was stirred at room temperature for 1 hour. The solvent was then evaporated and residue was pumped dry. The residue was redissolved in methylene chloride (5 mL) and dibenzyl (5-aminopentane-1,4-diyl)(S)-dicarbamate (Intermediate A) (87 mg, 0.23 mmol) and triethylamine (60 μL, 0.40 mmol) was added. The reaction was allowed to stir at room temperature overnight. The reaction mixture was then dissolved in saturated sodium bicarbonate and extracted with methylene chloride. The combined organic layers were then dried over sodium sulfate and purified using an ISCO chromatograph with silica chromatograph with silica (0-10% MeOH/methylene chloride) to give product was a white solid (70 mg, 48% yield). $^1$H NMR ($CDCl_3$) (300 MHz) δ 8.00 (s, 2H), 7.94 (s, 1H), 7.69 (m, 4H), 7.50-7.41 (m, 5H), 7.31 (m, 5H), 7.23 (m, 5H), 5.05 (s, 4H), 3.9 (m, 1H), 3.57 (m, 2H), 3.23 (m, 2H), 1.64 (m, 4H).

EXAMPLE 12

Preparation of (S)-5-([1,1':3',1"-terphenyl]-5'-carboxamido)pentane-1,2-diaminium chloride

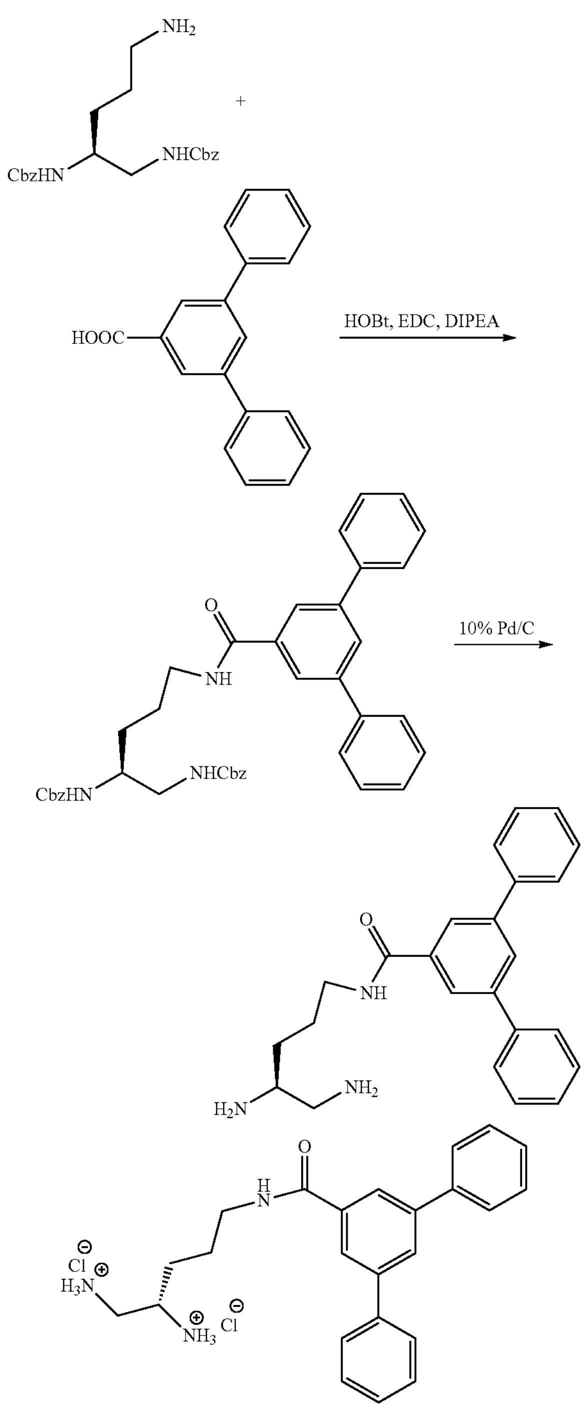

(S)-5-([1,1′:3′,1″-Terphenyl]-5′-carboxamido)pentane-1,2-diaminium

A suspension of dibenzyl (5-([1,1':3',1'-terphenyl]-5'-carboxamido)pentane-1,2-diyl)(S)-dicarbamate (80 mg, 0.125 mmol), 10% Pd/C (20 mg) in methanol (15 mL) was purged and stirred under a hydrogen atmosphere for overnight. After all of the starting material was consumed, the catalyst was filtered through Celite. The filtrate was added with 0.5 mL of 4N HCl in dioxane and was stirred at room temperature for 10 minutes. The solvent was removed to give a residue which was then triturated with ethyl acetate to afford the pure product as white solid (43 mg, 77% yield); $^{1}$H NMR (300 MHz, DMSO-$d_6$) δ 8.94 (m, 1H), 8.57 (m, 5H), 8.18 (m, 2H), 8.08 (s, 1H), 7.88 (m, 4H), 7.57-7.43 (m, 6H), 3.40 (m, 3H), 3.14 (m, 2H), 1.76 (m, 4H).

The requisite intermediate was prepared as follows:

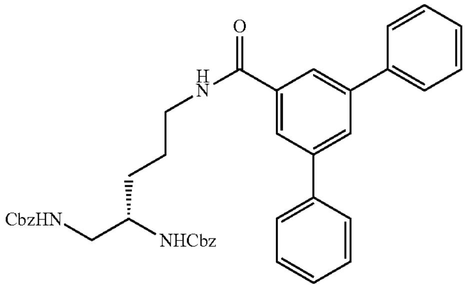

Dibenzyl (5-([1,1′:3′,1″-terphenyl]-5′-carboxamido)pentane-1,2-diyl)(S)-dicarbamate

[1,1':3',1"-Terphenyl]-5'-carboxylic acid (100 mg, 0.37 mmol) was dissolved in dry DMF (1.0 mL) and DIPEA (190 μL, 1.10 mmol), HOBt (30 mg, 0.22 mmol), EDC (140 mg, 0.730 mmol) were added. The reaction mixture was stirred at room temperature for 5 minutes. Dibenzyl (5-aminopentane-1,2-diyl)(S)-dicarbamate (Intermediate D) (212 mg, 0.37 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (182 mg, 77% yield). LC/MS: 642.4 (M+H).

Preparation of Intermediate D (dibenzyl (5-aminopentane-1,2-diyl)(S)-dicarbamate)

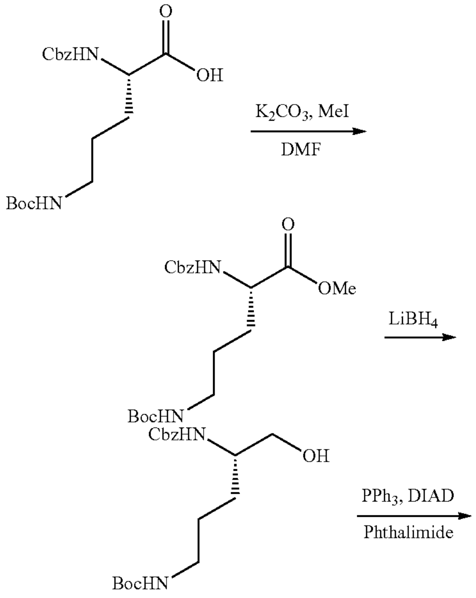

-continued

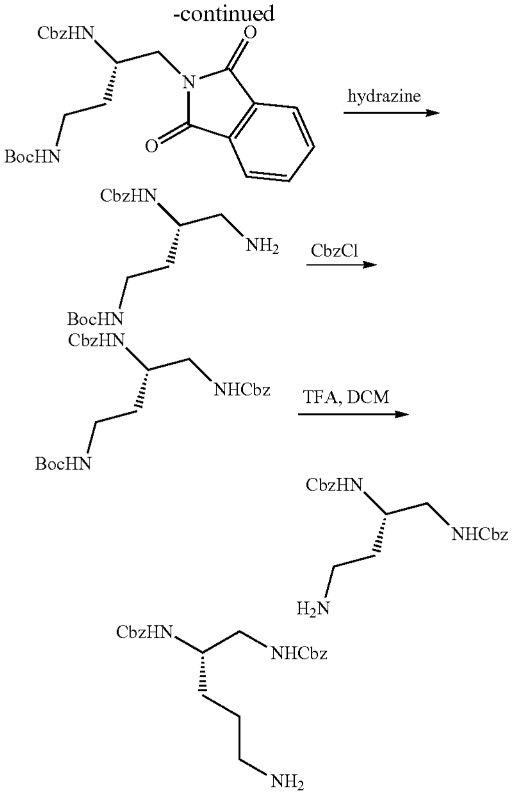

Dibenzyl (5-aminopentane-1,2-diyl)(S)-dicarbamate

Dibenzyl t-butyl pentane-1,2,5-triyl(S)-tricarbamate (189 mg, 0.39 mmol) was dissolved in DCM (3 mL) and the reaction mixture cooled to 0° C. under nitrogen. TFA (2 mL) was added and the reaction stirred at that temperature for 3 hours. On completion of the reaction, the reaction was quenched with saturated solution of $NaHCO_3$ and extracted with DCM. The organic layer was concentrated under reduced pressure to give product as a white solid. (101.7 mg, 67%); 1H NMR ($CDCl_3$) (400 MHz) δ 7.17 (m, 10H), 5.51 (m, 1H), 4.90 (m, 4H), 3.54 (m, 4H), 3.05 (m, 2H), 2.84 (m, 2H), 1.43 (m, 4H); $^{13}$C NMR δ 161.3, 160.9, 160.5, 160.1, 158.0, 157.6, 135.7, 135.1, 128.6, 128.3, 127.7, 119.5, 116.6, 113.7, 68.3, 67.4, 51.2, 44.6, 39.9, 28.6, 23.4.

The requisite intermediates were prepared as follows:

Step 1)

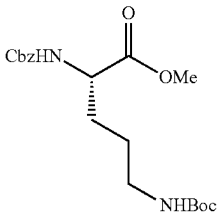

Methyl (S)-2-(((benzyloxy)carbonyl)amino)-5-((t-butoxycarbonyl)amino)pentanoate (S)-2-(((Benzyloxy)carbonyl)amino)-5-((t-butoxycarbonyl)amino)pentanoic acid (1.0 g, 2.73 mmol) was dissolved in DMF (5 mL) and $K_2CO_3$ (453 mg, 3.26 mmol). The reaction was cooled to 0° C. and methyl iodide (775 mg, 5.46 mmol) was added. The reaction was allowed to warm to room temperature and stirred at the temperature overnight. Then the reaction mixture was washed with saturated sodium bicarbonate solution and extracted with ethyl acetate. The combined organic layers were washed with brine, dried over sodium sulfate, concentrated and purified on ISCO (0-60% ethyl acetate/Hexane) to give product as a colorless oil. (761 mg, 73%); $^{1}$H NMR ($CDCl_3$) δ 7.19 (s, 5H), 6.06 (d, 1H, J=8), 5.12 (brs, 1H), 4.94 (s, 2H), 4.17 (m, 1H), 3.55 (s, 3H), 2.94 (m, 2H), 1.69 (m, 1H), 1.55 (m, 1H), 1.40 (m, 2H), 1.27 (s, 9H); $^{13}$C NMR δ 172.7, 156.0, 155.9, 136.3, 128.2, 128.1, 127.9, 127.8, 78.6, 67.2, 66.5, 53.7, 39.8, 29.2, 28.2, 25.9.

Step 2)

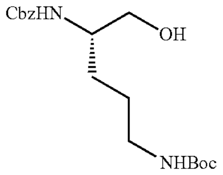

Benzyl t-butyl (5-hydroxypentane-1,4-diyl)(S)-dicarbamate

To a solution of methyl (S)-2-(((benzyloxy)carbonyl)amino)-5-((t-butoxycarbonyl)amino)pentanoate (431 mg, 1.13 mmol) in THF (5 mL)/ethanol (1 mL) was added $LiBH_4$ (32 mg, 1.47 mmol) at 0° C. The mixture was stirred at that temperature for 30 minutes and warmed to room temperature and stirred for overnight. The reaction mixture was poured into water and extracted with ethyl acetate. The combine organic layers were washed with brine and dried over sodium sulfate and concentrated. It was purified on ISCO (0-70% ethyl acetate/hexane to give product as a colorless oil. (385 mg, 97%); $^{1}$H NMR ($CDCl_3$) (400 MHz) δ 7.28 (m, 5H), 5.02 (s, 3H), 3.60 (m, 4H), 3.04 (m, 2H), 1.47 (m, 4H), 1.36 (m, 9H); $^{13}$C NMR δ 156.6, 156.1, 136.4, 128.5, 128.1, 128.0, 79.3, 66.8, 65.0, 62.7, 52.9, 52.4, 40.3, 29.8, 28.4, 26.7, 26.0.

Step 3)

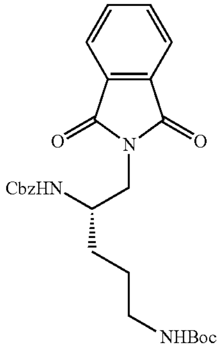

Benzyl t-butyl
(5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and overnight at room temperature. The mixture was concentrated under reduced pressure and residue purified using an ISCO chromatograph (0-70% ethyl acetate/hexane) to give product as a white solid. (340 mg, 69%); $^{1}$H NMR ($CDCl_3$) (400 MHz) δ 7.82 (m, 2H), 7.71 (m, 2H), 7.27 (m, 5H), 5.18 (brs, 1H), 4.96 (m, 2H), 4.67 (brs, 1H), 4.02 (m, 1H) 3.75 (m, 2H), 3.14 (m, 2H), 1.55 (m, 4H), 1.44 (s, 9H); $^{13}$C NMR δ 168.4, 156.3, 156.0, 136.6, 133.9, 131.8, 128.4, 128.3, 127.8, 127.7, 123.3, 78.9, 66.3, 60.3, 50.7, 41.9, 40.2, 29.9, 28.4, 26.4.

Step 4)

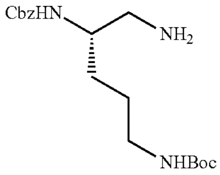

Benzyl t-butyl (5-aminopentane-1,4-diyl)(S)-dicarbamate

The phthalimide (340 mg, 0.71 mmol) formed was dissolved in methanol (20 mL) and hydrazine monohydrate (0.07 mL, 1.41 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO chromatograph using (0-10% Methanol/DCM+1% $NH_4OH$) to give product as a white powder. (164 mg, 66%); $^{1}$H NMR ($CDCl_3$) (400 MHz) δ 7.25 (m, 5H), 5.41 (d, 1H, J=8), 5.00 (s, 1H), 4.84 (brs, 1H); 3.50 (m, 1H), 3.01 (m, 2H), 2.61 (m, 2H), 1.40 (m, 4H), 1.36 (s, 9H); $^{13}$C NMR δ 156.6, 156.0, 136.6, 128.4, 128.1, 128.0, 78.9, 66.6, 53.2, 45.7, 40.2, 29.7, 28.4, 26.6, 25.0, 24.9.

Step 5)

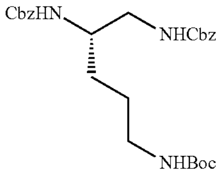

Dibenzyl t-butyl pentane-1,2,5-triyl)(S)-tricarbamate

Benzyl t-butyl (5-aminopentane-1,4-diyl)(S)-dicarbamate (162.2 mg, 0.46 mmol) was dissolved in DCM (5 mL) under nitrogen atmosphere and triethylamine (0.08 mL, 0.55 mmol) was added. CbzCl (0.08 mL, 0.55 mmol) was added and reaction stirred at room temperature until the end of the reaction as determined by TLC. The DCM was concentrated under reduced pressure and the residue purified on an ISCO chromatograph to give product as a white solid (126 mg, 57%); $^{1}$H NMR ($CDCl_3$) (400 MHz) δ 7.34 (m, 10), 5.36 (m, 1H), 5.23 (d, IH, J=4), 5.09 (s, 4H), 4.72 (m, 1H), 3.72 (m, 1H), 3.21 (m, 4H), 1.45 (m, 4H), 1.42 (s, 9H); $^{13}$C NMR δ 157.0, 156.5, 156.1, 136.4, 128.5, 128.1, 128.07, 128.0, 79.1, 66.8, 66.7, 51.7, 45.0, 40.1, 29.5, 28.4, 26.4.

EXAMPLE 13

Preparation of (S)-5-(4,4"-difluoro-[1,1':3',1"-terphenyl]-5'-carboxamido)pentane-1,4-diaminium chloride

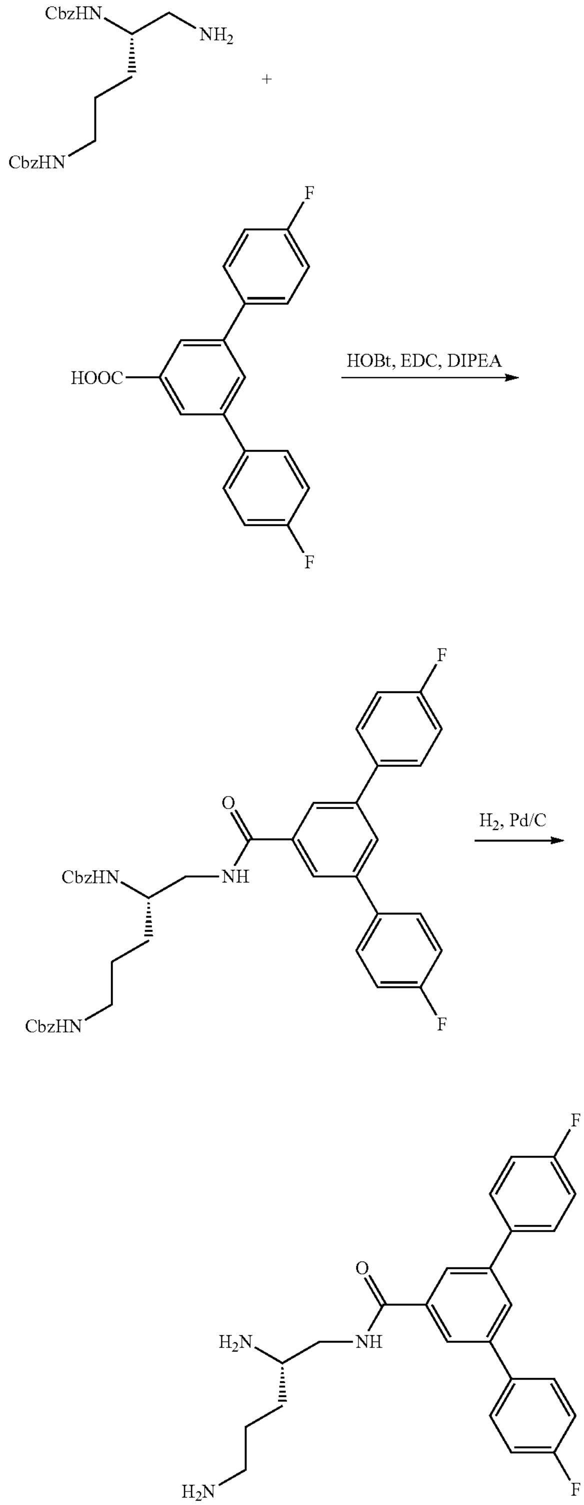

-continued

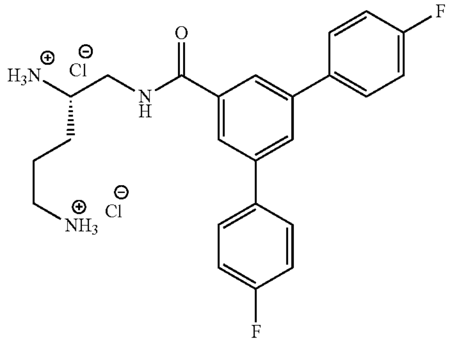

(S)-5-(4,4″-Difluoro-[1,1′:3′,1″-terphenyl]-5′-carboxamido)pentane-1,4-diaminium chloride A suspension of dibenzyl (5-(4,4"-difluoro-[1,1':3',1"-terphenyl]-5'-carboxamido)pentane-1,4-diyl)(S)-dicarbamate (100 mg, 0.15 mmol), 10% Pd/C (20 mg) in methanol (15 mL) was purged and stirred under a hydrogen atmosphere for overnight. After all starting material was consumed; the catalyst was filtered through celite. The filtrate was added with 0.5 mL of 4N HCl in dioxane and was stirred at room temperature for 10 minutes. The solvent was removed to give a residue which was then triturated with ethyl acetate to afford the pure product as white solid (47 mg, 67% yield); $^1$H NMR (300 MHz, DMSO-d6) δ 9.13 (m, 1H), 8.29-8.09 (m, 5H), 8.09 (s, 1H), 7.96 (m, 7H), 7.37 (m, 4H), 3.61 (m, 2H), 3.46 (m, 1H), 2.86 (m, 2H), 1.76 (m, 4H).

The requisite intermediate was prepared as follows:

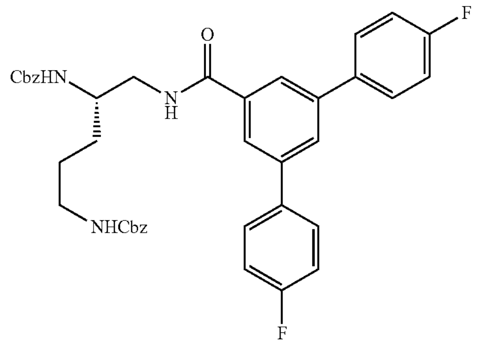

Dibenzyl (5-(4,4″-difluoro-[1,1′:3′,1″-terphenyl]-5′-carboxamido)pentane-1,4-diyl)(S)-dicarbamate 4,4"-Difluoro-[1,1':3',1"-terphenyl]-5'-carboxylic acid (80 mg, 0.26 mmol) was dissolved in dry DMF (1.0 mL) and DIPEA (90 μL, 0.58 mmol), HOBt (21.1 mg, 0.16 mmol), EDC (59.6 mg, 0.31 mmol) were added. The reaction mixture was stirred at room temperature for 5 minutes. Dibenzyl (5-aminopentane-1,4-diyl)(S)-dicarbamate (Intermediate A) (100 mg, 0.26 mmol) was added at room temperature and the reaction was continued to stir overnight. The reaction mixture was then diluted with ethyl acetate and washed with saturated $NaHCO_3$ and brine. The organic layer was dried over sodium sulfate and filtered. Filtrate was then concentrated and purified using an ISCO chromatograph with silica (hexane/ethyl acetate) to give the product (115 mg, 74% yield). LC/MS: 678.2 (M+H).

EXAMPLE 14

Preparation of Intermediate E (benzyl (-butyl (3-aminopropane-1,2-diyl)(R)-dicarbamate)

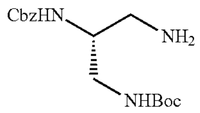

Benzyl t-butyl (3-aminopropane-1,2-diyl)(R)-dicarbamate

Benzyl t-butyl (3-(1,3-dioxoisoindolin-2-yl)propane-1,2-diyl)(S)-dicarbamate (450 mg, 0.99 mmol) was dissolved in methanol (10 mL) and hydrazine monohydrate (0.1 mL, 1.98 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO chromatograph with silica (0-10% Methanol/DCM+1% $NH_4OH$) to give product as a colorless oil. (140 mg, 44%); $^1$H NMR ($CDCl_3$, 400 MHz) δ 7.27 (m, 5H), 6.37 (s, 1H), 5.87 (s, 1H), 5.02 (s, 2H), 3.94 (s, 4H), 3.60 (m, 1H), 3.12 (m, 2H), 2.70 (m, 2H), 1.36 (s, 9H).

The requisite intermediates were prepared as follows:

Step 1) Benzyl t-butyl (3-hydroxypropane-1,2-diyl)(S)-dicarbamate

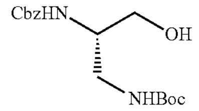

Benzyl t-butyl (3-hydroxypropane-1,2-diyl)(S)-dicarbamate

To a solution of (S)-2-(((benzyloxy)carbonyl)amino)-3-((t-butoxycarbonyl)amino)propanoic acid (900 mg, 2.66 mmol) in DME (10 mL) at −15° C. were successively added a solution of N-methyl morpholine (0.33 mL, 3 mmol) and isobutyl chloroformate (0.35 mL, 2.66 mmol). The reaction was stirred at −15 to −10° C. for 15 minutes. The precipitated N-methyl morpholine HCl was removed by filtration and washed with DME (10 mL), the combine filtrates were chilled to −15° C. in an ice-salt bath. Then a solution of sodium borohydride (301 mg, 7.98 mmol) in water (5 mL) was added in one portion at −15° C. This reaction mixture was stirred at this temperature for 10 minutes. The reaction was quenched by the addition of saturated aqueous $NH_4Cl$ and the resulting mixture was extracted with ethyl acetate. The organic layer was washed with brine and dried over sodium sulfate. The solution was then filtered and concentrated in vacuo, purified on column (0-70% ethyl acetate/hexane) to give product as a white powder (675 mg, 78%); $^1$H NMR ($CDCl_3$) (400 MHz) (MeOD) δ 7.34 (m, 5H), 5.09 (s, 2H), 3.73 (m, 1H), 3.24 (m, 4H), 1.44 (s, 9H); $^{13}$C NMR δ 158.6, 138.3, 129.5, 129.0, 128.9, 80.3, 67.5, 63.0, 54.6, 42.1, 28.8.

Step 2) Benzyl t-butyl (3-(1,3-dioxoisoindolin-2-yl) propane-1,2-diyl)(S)-dicarbamate

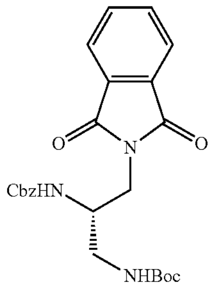

Benzyl t-butyl (3-(1,3-dioxoisoindolin-2-yl)propane-1,2-diyl)(S)-dicarbamate

Triphenylphosphine (709 mg, 2.71 mmol) and phthalimide (398 mg, 2.71 mmol) were added to a flask containing dry THF (6 mL). Benzyl t-butyl (3-hydroxypropane-1,2-diyl)(S)-dicarbamate (730 mg, 2.26 mmol) was added and the flask was cooled to 0° C. DIAD (548 mg, 2.71 mmol) was added dropwise and reaction allowed to stir for 30 minutes at 0° C. and overnight at room temperature. The mixture was concentrated under reduced pressure and residue purified on an ISCO chromatograph with silica (0-70% ethyl acetate/hexane) to give the product as a white solid. (556 mg, 55%); NMR ($CDCl_3$) (400 MHz) δ 7.83 (m, 2H), 7.71 (m, 2H), 7.28 (m, 5H), 5.70 (m, 1H), 5.26 (m, 1H), 5.02 (s, 2H), 4.06 (m, 1H), 3.84 (m, 2H), 3.31 (m, 2H), 1.44 (s, 9H), $^{13}$C NMR δ 168.5, 156.6, 156.3, 136.4, 134.1, 131.8, 128.3, 127.9, 123.4, 79.7, 66.6, 51.6, 41.9, 39.2, 28.3, 21.9.

EXAMPLE 15

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

I

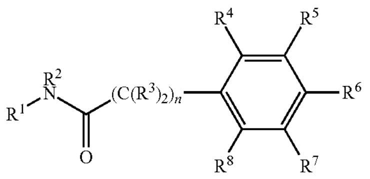

wherein:

$R^1$ is $(C_3-C_8)$alkyl substituted with two or more groups selected from —$NR^{b1}R^{c1}$;

$R^2$ is hydrogen or $(C_1-C_3)$alkyl;

each $R^3$ is independently hydrogen, halo or $(C_1-C_4)$alkyl;

$R^4$ is hydrogen, halo, $(C_1-C_6)$alkyl, $(C_1-C_6)$haloalkyl, $(C_1-C_6)$alkoxy, $(C_1-C_4)$haloalkoxy, or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^5$ is hydrogen, halo, $(C_1-C_6)$alkyl, $(C_1-C_6)$haloalkyl, $(C_1-C_6)$alkoxy, $(C_1-C_4)$haloalkoxy, or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^6$ is hydrogen, halo, $(C_1-C_6)$alkyl, $(C_1-C_6)$haloalkyl, $(C_1-C_6)$alkoxy, $(C_1-C_4)$haloalkoxy, or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^7$ is hydrogen, halo, $(C_1-C_6)$alkyl, $(C_1-C_6)$haloalkyl, $(C_1-C_6)$alkoxy, $(C_1-C_4)$haloalkoxy, or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^8$ is hydrogen, halo, $(C_1-C_6)$alkyl, $(C_1-C_6)$haloalkyl, $(C_1-C_6)$alkoxy, $(C_1-C_4)$haloalkoxy, or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

each $R^{b1}$ and $R^{c1}$ is independently hydrogen or $(C_1-C_4)$ alkyl; and n is 0 or 1;

or a salt thereof;

provided at least one of $R^4$, $R^5$, or $R^6$ is not hydrogen.

2. The compound of claim 1, wherein $R^2$ is hydrogen and each $R^3$ is hydrogen.

3. The compound of claim 1, wherein $R^8$ is hydrogen.

4. The compound of claim 1, wherein $R^4$ is hydrogen, $(C_1-C_6)$haloalkyl or aryl wherein the aryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

5. The compound of claim 1, wherein $R^6$ is $(C_1-C_6)$ haloalkyl or hydrogen.

6. The compound of claim 1, wherein $R^5$ is $(C_1-C_6)$alkyl, $(C_1-C_6)$haloalkyl, or phenyl wherein phenyl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

7. The compound of claim 1, wherein $R^7$ is $(C_1-C_6)$alkyl, $(C_1-C_6)$haloalkyl, or phenyl wherein phenyl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

8. The compound of claim 1, wherein the moiety:

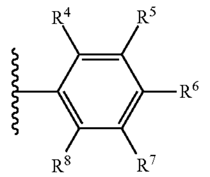

of the compound of formula I is:
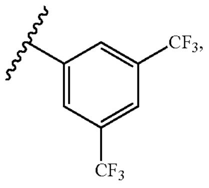
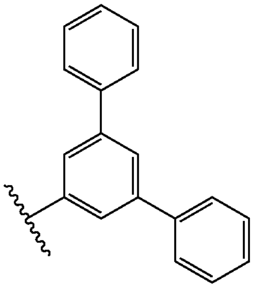
,
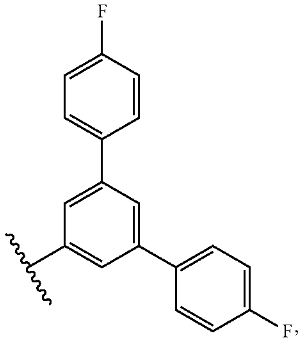
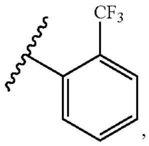
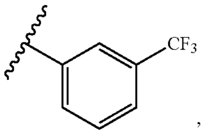
,
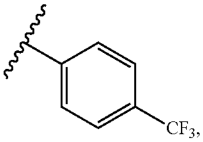
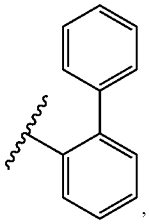
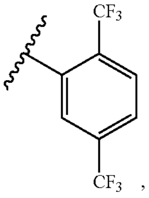
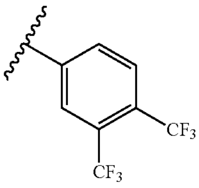
or
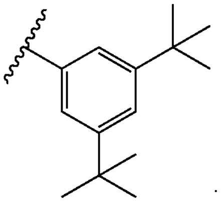
.
9. The compound of claim 1, wherein $R^1$ is $(C_3\text{-}C_8)$alkyl substituted with two groups independently selected from —$NR^{b1}R^{c1}$.
10. The compound of claim 1, wherein $R^1$ is:
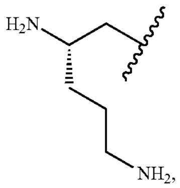
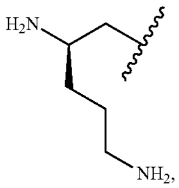
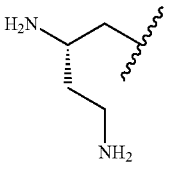
,
-continued
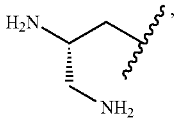
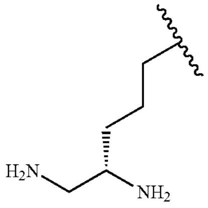
or
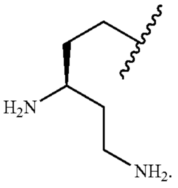
11. The compound of claim 1, wherein n is 0.
12. The compound of claim 1 which is:
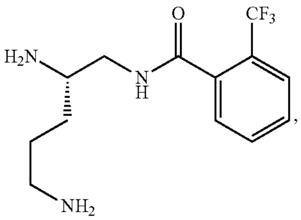
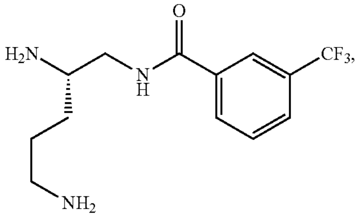
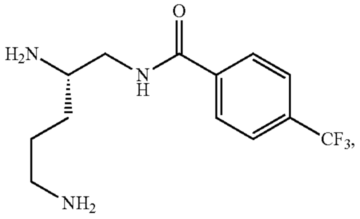
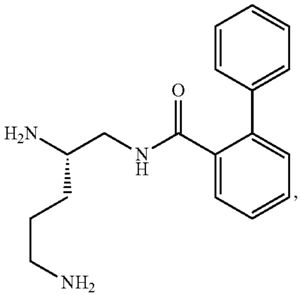
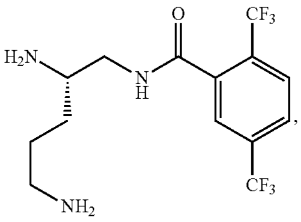

-continued

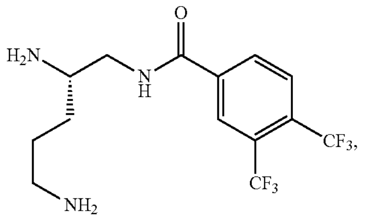

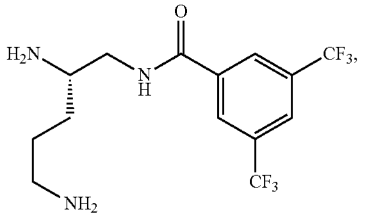

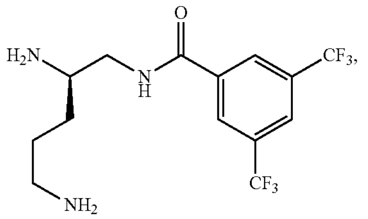

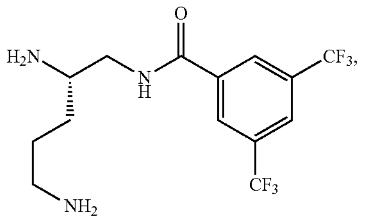

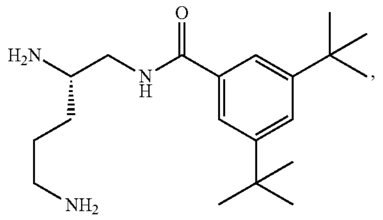

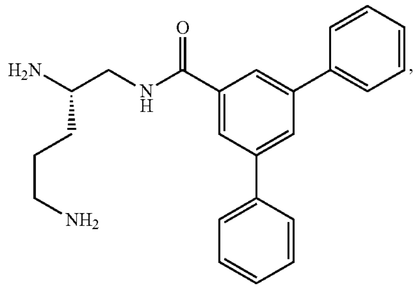

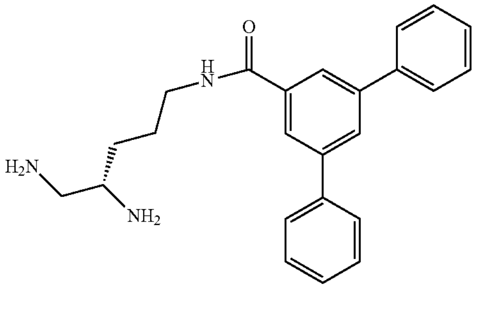

or

-continued

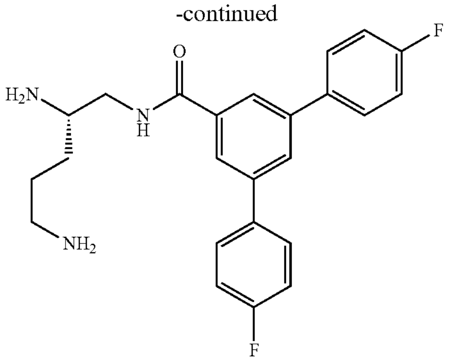

or a salt thereof.

13. A compound of formula I:

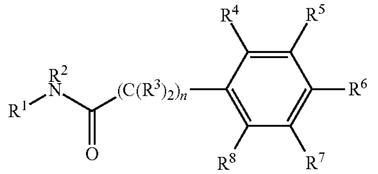

I wherein:

$R^1$ is $(C_3\text{-}C_8)$alkyl substituted with two or more groups selected from —$NR^{b1}R^{c1}$;

$R^2$ is hydrogen or $(C_1\text{-}C_3)$alkyl;

each $R^3$ is independently hydrogen, halo or $(C_1\text{-}C_4)$alkyl;

$R^4$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^5$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^6$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^7$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^8$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

each $R^{b1}$ and $R^{c1}$ is independently hydrogen or $(C_1\text{-}C_4)$alkyl; and n is 0 or 1;

or a salt thereof.

14. A compound of formula I:

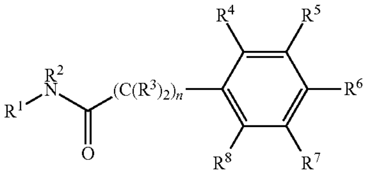

I wherein:

$R^1$ is $(C_3\text{-}C_8)$alkyl substituted with two or more groups selected from —$NR^{b1}R^{c1}$;

$R^2$ is hydrogen or $(C_1\text{-}C_3)$alkyl;

each $R^3$ is independently hydrogen, halo or $(C_1\text{-}C_4)$alkyl;

$R^4$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^5$ is halo, $(C_1\text{-}C_6)$alkyl, $(C_1\text{-}C_6)$haloalkyl, $(C_1\text{-}C_6)$ alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$ haloalkyl, $(C_1\text{-}C_4)$alkoxy and $(C_1\text{-}C_4)$haloalkoxy;

$R^6$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^7$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^8$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

each $R^{a1}$ is independently hydrogen or $(C_1\text{-}C_4)$alkyl; and n is 0 or 1;

or a salt thereof.

15. A compound of formula I:

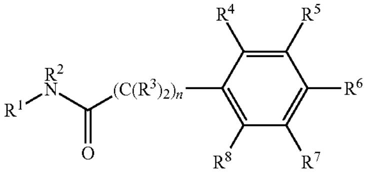

I wherein:

$R^1$ is $(C_3\text{-}C_8)$alkyl substituted with two or more groups selected from —$NR^{b1}R^{c1}$;

$R^2$ is hydrogen or $(C_1\text{-}C_3)$alkyl;

each $R^3$ is independently hydrogen, halo or $(C_1\text{-}C_4)$alkyl;

$R^4$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^5$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^6$ is halo, $(C_1\text{-}C_6)$alkyl, $(C_1\text{-}C_6)$haloalkyl, $(C_1\text{-}C_6)$ alkoxy, $(C_1\text{-}C_4)$haloalkoxy or aryl wherein the aryl is optionally substituted with one or more groups independently selected from halo, $(C_1\text{-}C_4)$alkyl, $(C_1\text{-}C_4)$ haloalkyl, $(C_1\text{-}C_4)$alkoxy and $(C_1\text{-}C_4)$haloalkoxy;

$R^7$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

$R^8$ is hydrogen, halo, $(C_1\text{-}C_6)$alkyl, $(C_1\text{-}C_6)$haloalkyl, $(C_1\text{-}C_6)$alkoxy, $(C_1\text{-}C_4)$haloalkoxy, or aryl wherein the aryl is optionally substituted with one or more groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

each $R^{b1}$ and $R^{c1}$ is independently hydrogen or $(C_1\text{-}C_4)$ alkyl; and n is 0 or 1;

or a salt thereof.

16. A pharmaceutical composition comprising a compound of formula I or a pharmaceutically acceptable salt thereof as described in claim 1, and a pharmaceutically acceptable vehicle.

17. A pharmaceutical composition comprising a compound of formula I or a pharmaceutically acceptable salt thereof as described in claim 1, one or more antibacterial agents and a pharmaceutically acceptable vehicle.

18. A method of inhibiting a bacterial efflux pump in an animal comprising administering to the animal a compound of formula I or a pharmaceutically acceptable salt thereof as described in claim 1.

19. A method of treating or preventing a bacterial infection in an animal comprising co-administering to the animal a compound of formula I or a pharmaceutically acceptable salt thereof as described in claim 1 and one or more antibacterial agents.

20. The method of claim 19 wherein the animal is infected with bacteria.

21. The method of claim 20 wherein the bacterial infection is a Gram-negative bacterial strain infection.

22. The method of claim 21, wherein the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kin-*

*gella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

23. The method of claim 20, wherein the bacterial infection is a Gram-positive bacterial strain infection.

24. The method of claim 23, wherein the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis*.

* * * * *

UNITED STATES PATENT AND TRADEMARK OFFICE

CERTIFICATE OF CORRECTION

PATENT NO. : 9,926,261 B2
APPLICATION NO. : 15/066911
DATED : March 27, 2018
INVENTOR(S) : Edmond J. LaVoie et al.

It is certified that error appears in the above-identified patent and that said Letters Patent is hereby corrected as shown below:

In the Claims

Column 79, Line 43, Claim 14, please delete "each $R^{a1}$ is independently hydrogen or $(C_1-C_4)$alkyl;" and insert -- each $R^{b1}$ and $R^{c1}$ is independently hydrogen or $(C_1-C_4)$alkyl; -- therefor.

Signed and Sealed this
Twenty-fourth Day of July, 2018

Andrei Iancu
*Director of the United States Patent and Trademark Office*